(12) United States Patent
Thi Tieu et al.

(10) Patent No.: US 10,314,634 B2
(45) Date of Patent: Jun. 11, 2019

(54) CATHETER DEVICE WITH LONGITUDINALLY EXPANDING INTERIOR COMPONENTS FOR COMPRESSING CANCELLOUS BONE

(71) Applicant: AVANTEC VASCULAR CORPORATION, Sunnyvale, CA (US)

(72) Inventors: Yen Hai Thi Tieu, Sunnyvale, CA (US); Kim Phan, Sunnyvale, CA (US); Nicholas DeBeer, Sunnyvale, CA (US)

(73) Assignee: AVANTEC VASCULAR CORPORATION, Sunnyvale, CA (US)

( * ) Notice: Subject to any disclaimer, the term of this patent is extended or adjusted under 35 U.S.C. 154(b) by 612 days.

(21) Appl. No.: 14/931,787

(22) Filed: Nov. 3, 2015

(65) Prior Publication Data
US 2016/0120584 A1   May 5, 2016

Related U.S. Application Data

(60) Provisional application No. 62/074,781, filed on Nov. 4, 2014.

(51) Int. Cl.
*A61B 17/88* (2006.01)
(52) U.S. Cl.
CPC ............... *A61B 17/8855* (2013.01)
(58) Field of Classification Search
CPC ... A61B 17/88; A61B 17/885; A61B 17/8852; A61B 17/8855; A61B 17/8858
See application file for complete search history.

(56) References Cited

U.S. PATENT DOCUMENTS

| | | |
|---|---|---|
| 3,952,737 A | 4/1976 | Kimmell, Jr. |
| 4,085,743 A | 4/1978 | Yoon |
| 4,174,715 A | 11/1979 | Hasson |
| 4,467,802 A | 8/1984 | Maslanka |
| 4,611,594 A | 9/1986 | Grayhack et al. |
| 4,655,219 A | 4/1987 | Petruzzi |
| 4,723,936 A | 2/1988 | Buchbinder et al. |
| 4,873,978 A | 10/1989 | Ginsburg |
| 4,960,411 A | 10/1990 | Buchbinder |
| 5,011,488 A | 4/1991 | Ginsburg |
| 5,041,093 A | 8/1991 | Chu |
| 5,074,845 A | 12/1991 | Miraki et al. |
| 5,098,440 A | 3/1992 | Hillstead |
| 5,102,415 A | 4/1992 | Guenther et al. |
| 5,549,626 A | 8/1996 | Miller et al. |
| 5,601,595 A | 2/1997 | Smith |

(Continued)

FOREIGN PATENT DOCUMENTS

| | | |
|---|---|---|
| EP | 1172073 A1 | 1/2002 |
| JP | H 10-509623 A | 9/1998 |

(Continued)

OTHER PUBLICATIONS

WO, PCT/US2014/042343 ISR and Written Opinion, dated Sep. 30, 2014.

(Continued)

*Primary Examiner* — Eric S Gibson
(74) *Attorney, Agent, or Firm* — One LLP

(57) ABSTRACT

Systems, devices, and methods are provided for a catheter device for use in a medical procedure wherein the interior of the catheter device expands to accommodate longitudinal expansion of the expandable member to compress cancellous bone.

10 Claims, 26 Drawing Sheets

(56) References Cited

U.S. PATENT DOCUMENTS

| | | |
|---|---|---|
| 5,653,684 A | 8/1997 | Laptewicz et al. |
| 5,662,671 A | 9/1997 | Barbut et al. |
| 5,746,251 A | 5/1998 | Bullard |
| 5,782,747 A | 7/1998 | Zimmon |
| 5,800,457 A | 9/1998 | Gelbfish |
| 5,814,064 A | 9/1998 | Daniel et al. |
| 5,827,324 A | 10/1998 | Cassell et al. |
| 5,846,251 A | 12/1998 | Hart |
| 5,908,435 A | 6/1999 | Samuels |
| 5,911,734 A | 6/1999 | Tsugita et al. |
| 5,944,728 A | 8/1999 | Bates |
| 6,001,118 A | 12/1999 | Daniel et al. |
| 6,156,055 A | 12/2000 | Ravenscroft |
| 6,159,230 A | 12/2000 | Samuels |
| 6,203,561 B1 | 2/2001 | Ramee et al. |
| 6,210,370 B1 | 4/2001 | Chi-Sing et al. |
| 6,238,412 B1 | 5/2001 | Dubrul et al. |
| 6,251,092 B1 | 6/2001 | Qin et al. |
| 6,264,671 B1 | 7/2001 | Stack et al. |
| 6,290,710 B1 | 9/2001 | Cryer et al. |
| 6,306,163 B1 | 10/2001 | Fitz |
| 6,336,934 B1 | 1/2002 | Gilson et al. |
| 6,395,017 B1 | 5/2002 | Dwyer et al. |
| 6,443,972 B1 | 9/2002 | Bosma et al. |
| 6,447,531 B1 | 9/2002 | Amplatz |
| 6,458,151 B1 | 10/2002 | Saltiel |
| 6,485,501 B1 | 11/2002 | Green |
| 6,500,182 B2 | 12/2002 | Foster |
| 6,569,184 B2 | 5/2003 | Huter |
| 6,602,271 B2 | 8/2003 | Adams et al. |
| 6,605,102 B1 | 8/2003 | Mazzocchi et al. |
| 6,632,236 B2 | 10/2003 | Hogendijk |
| 6,645,222 B1 | 11/2003 | Parodi et al. |
| 6,663,652 B2 | 12/2003 | Daniel et al. |
| 6,679,893 B1 | 1/2004 | Tran |
| 6,695,813 B1 | 2/2004 | Boyle et al. |
| 6,699,260 B2 | 3/2004 | Dubrul et al. |
| 6,702,834 B1 | 3/2004 | Bpylan et al. |
| 6,743,247 B1 | 6/2004 | Levinson et al. |
| 6,780,196 B2 | 8/2004 | Chin et al. |
| 6,800,080 B1 | 10/2004 | Bates |
| 6,833,002 B2 | 12/2004 | Stack et al. |
| 6,896,690 B1 | 5/2005 | Lambrecht et al. |
| 6,958,074 B2 | 10/2005 | Russell |
| 7,211,089 B2 | 5/2007 | Kear et al. |
| 7,322,989 B2 | 1/2008 | Teague et al. |
| 7,338,512 B2 | 3/2008 | McGuckin, Jr. et al. |
| 7,377,925 B2 | 5/2008 | Poll |
| 7,491,210 B2 | 2/2009 | Dubrul et al. |
| 7,625,390 B2 | 12/2009 | Hendriksen et al. |
| 7,658,747 B2 | 2/2010 | Forde et al. |
| 7,731,723 B2 | 6/2010 | Kear et al. |
| 7,780,693 B2 | 8/2010 | Brady et al. |
| 7,780,694 B2 | 8/2010 | Palmer et al. |
| 7,837,702 B2 | 11/2010 | Bates |
| 7,993,362 B2 | 8/2011 | Lowe et al. |
| 8,038,704 B2 | 10/2011 | Sherburne |
| 8,043,322 B2 | 10/2011 | Hendriksen et al. |
| 8,202,309 B2 | 6/2012 | Styrc |
| 8,273,073 B2 | 9/2012 | Levine et al. |
| 8,298,244 B2 | 10/2012 | Garcia et al. |
| 8,469,969 B2 | 6/2013 | Kear et al. |
| 8,469,970 B2 | 6/2013 | Diamant |
| 8,475,488 B2 | 7/2013 | Cartier et al. |
| 8,512,401 B2 | 8/2013 | Murray, III et al. |
| 8,747,597 B2 | 6/2014 | Rosqueta et al. |
| 2001/0044595 A1 | 11/2001 | Reydel et al. |
| 2002/0010476 A1 | 1/2002 | Mulholland et al. |
| 2003/0176884 A1 | 9/2003 | Berrada et al. |
| 2003/0187474 A1 | 10/2003 | Keegan et al. |
| 2004/0049226 A1 | 3/2004 | Keegan et al. |
| 2004/0093012 A1 | 5/2004 | Cully et al. |
| 2004/0138677 A1 | 7/2004 | Little et al. |
| 2004/0153118 A1 | 8/2004 | Clubb et al. |
| 2004/0181237 A1 | 9/2004 | Forde et al. |
| 2004/0199202 A1 | 10/2004 | Dubrul et al. |
| 2005/0159770 A1 | 7/2005 | Divani et al. |
| 2005/0182439 A1 | 8/2005 | Lowe |
| 2005/0187570 A1 | 8/2005 | Nguyen et al. |
| 2005/0234502 A1 | 10/2005 | Gilson et al. |
| 2005/0267515 A1 | 12/2005 | Oliva et al. |
| 2006/0020256 A1 | 1/2006 | Bell et al. |
| 2006/0074446 A1 | 4/2006 | Gilson et al. |
| 2006/0247572 A1 | 11/2006 | McCartney |
| 2007/0005101 A1 | 1/2007 | Fahey et al. |
| 2007/0112374 A1 | 5/2007 | Paul et al. |
| 2007/0149996 A1 | 6/2007 | Coughlin |
| 2007/0173884 A1 | 7/2007 | Gilson et al. |
| 2007/0244504 A1 | 10/2007 | Keegan et al. |
| 2007/0282369 A1 | 12/2007 | Gilson et al. |
| 2009/0182370 A1 | 7/2009 | Volobuyev et al. |
| 2009/0192485 A1 | 7/2009 | Heuser |
| 2009/0198315 A1 | 8/2009 | Boudjemline |
| 2009/0222035 A1 | 9/2009 | Schneiderman |
| 2009/0248060 A1 | 10/2009 | Schneider et al. |
| 2009/0287291 A1 | 11/2009 | Becking et al. |
| 2010/0137846 A1 | 6/2010 | Desai et al. |
| 2010/0256669 A1 | 10/2010 | Harris et al. |
| 2010/0312268 A1 | 12/2010 | Belson |
| 2010/0331949 A1 | 12/2010 | Habib |
| 2011/0040321 A1 | 2/2011 | Cartier |
| 2011/0046611 A1 | 2/2011 | Christiansen |
| 2011/0125180 A1 | 5/2011 | Tripp et al. |
| 2011/0178547 A1 | 7/2011 | Paul, Jr. et al. |
| 2011/0282274 A1 | 11/2011 | Fulton, III |
| 2011/0288572 A1 | 11/2011 | Martin |
| 2011/0307002 A1 | 12/2011 | Gilson et al. |
| 2012/0041473 A1 | 2/2012 | Nigon |
| 2013/0197567 A1 | 8/2013 | Brady et al. |
| 2013/0267848 A1 | 10/2013 | Fearmot et al. |
| 2013/0289694 A1 | 10/2013 | Sherburne |
| 2014/0005712 A1 | 1/2014 | Martin |
| 2014/0024887 A1 | 1/2014 | Ishii et al. |
| 2014/0155930 A1 | 6/2014 | Bennett et al. |
| 2014/0373334 A1 | 12/2014 | Gamarra et al. |
| 2015/0105819 A1 | 4/2015 | Becking et al. |
| 2015/0366650 A1 | 12/2015 | Zi et al. |

FOREIGN PATENT DOCUMENTS

| | | |
|---|---|---|
| JP | 2003-501203 A | 1/2003 |
| JP | 2004-524049 A | 8/2004 |
| JP | 2005-523767 A | 8/2005 |
| JP | 2007-508902 A | 4/2007 |
| JP | 2008-513121 A | 5/2008 |
| JP | 2008-514276 A | 5/2008 |
| JP | 4109422 B2 | 7/2008 |
| JP | 2009-517124 A | 4/2009 |
| JP | 4320142 B2 | 8/2009 |
| JP | 2013-154183 A | 8/2013 |
| KR | 101133157 B1 | 4/2012 |
| WO | WO 00/16846 A1 | 3/2000 |

OTHER PUBLICATIONS

WO, PCT/US2015/058898 ISR and Written Opinion, dated Feb. 11, 2016.

WO, PCT/US2015/065074 ISR and Written Opinion, dated Mar. 22, 2016.

WO, PCT/US2015/065025 ISR and Written Opinion, dated Apr. 1, 2016.

JP, 2016-519686 Official Action, dated Mar. 28, 2018.

WO, PCT/US2015/065102 ISR and Written Opinion, dated Sep. 8, 2016.

EP, 14810754.3 Extended Search Report, dated Nov. 14, 2016.

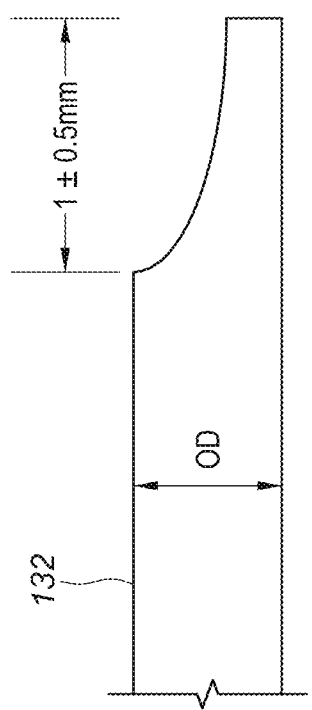

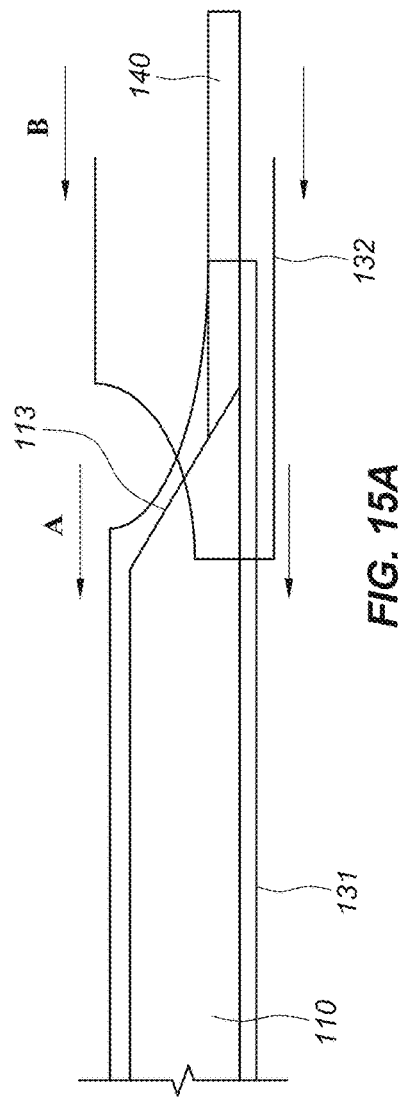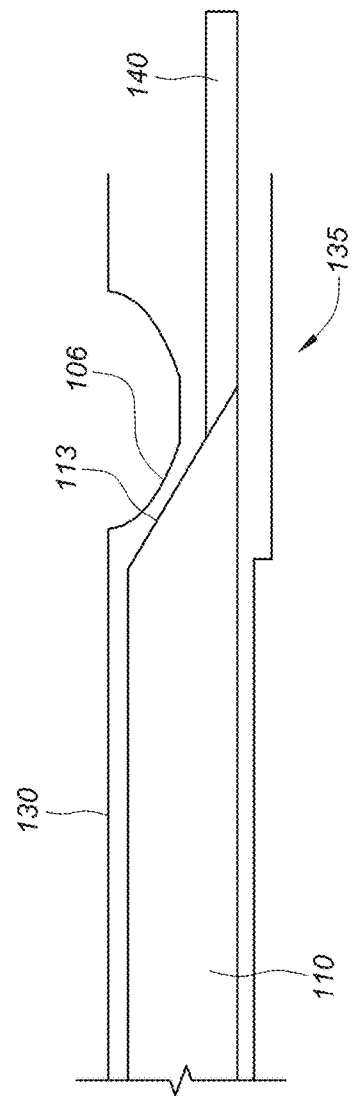

CATHETER DEVICE WITH LONGITUDINALLY EXPANDING INTERIOR COMPONENTS FOR COMPRESSING CANCELLOUS BONE

CROSS-REFERENCE TO RELATED APPLICATIONS

This application claims priority to and the benefit of U.S. Provisional Patent Application Ser. No. 62/074,781 filed Nov. 4, 2014, which is incorporated by reference herein in its entirety for all purposes.

FIELD

The subject matter described herein relates generally to catheter devices used in medical procedures.

BACKGROUND

Osseous tissue or bone tissue generally makes up the skeletal system of vertebrates. In humans, osseous tissue is made of cancellous bone and cortical bone. Cortical bone is generally solid and strong and provides a shell for cancellous bone which is also known as trabecular or spongy bone. In some humans cancellous bone may become diseased and lose mass and density, thus increasing risk of fractures or breaks in the bone. This decrease in bone mass and density is commonly referred to as osteoporosis and frequently affects the elderly. Medical procedures have been developed to treat osteoporosis and provide additional support to bones.

Some procedures require drilling through the cortical bone to treat the cancellous bone inside. Once a hole has been drilled in the cortical bone a catheter may be used to treat the cancellous bone. In some procedures a catheter with an expansion member, such as a balloon, near the end is introduced into the cancellous bone and the expansion member is expanded in order to compact the cancellous bone. After compacting the cancellous bone, a void in the cancellous bone is sometimes created and this void may be filled with bone cement to provide added strength for the bone.

Removal of a catheter with a balloon near its end can be complicated. Typically the balloon is deflated before removal from the hole in the cortical bone but problems may occur if, for example, the balloon is bulky in its deflated state or the balloon does not fully deflate before its attempted removal. A typical balloon inflates circumferentially as well as longitudinally from a deflated state closely wrapped to the underlying catheter body. In the case of longitudinal expansion the balloon may inflate beyond the distal tip of the catheter device. This can be problematic when extraction is attempted if the deflated balloon remains beyond the distal tip of the catheter device as the structure may be too bulky to pass through the cortical hole or to retract inside a cannula. As such, the development of devices with improved physical characteristics during medical procedures and ease of extraction following the medical procedures is advantageous.

SUMMARY

Provided herein are catheter devices for use in medical procedures and methods of using and manufacturing the devices. The devices are designed to provide ease of extraction after completion of the intended procedure. Systems and kits containing these devices are also provided herein. Although not limited to such, these devices, systems, and methods are described in the context of procedures for compacting cancellous bone. The catheter devices described herein preferably include multiple catheter tubes with a limited separable structure within an expandable member which may be delivered by a cannula. The configuration of these devices is described in detail by way of various embodiments which are only examples.

Other systems, devices, methods, features and advantages of the subject matter described herein will be or will become apparent to one with skill in the art upon examination of the following figures and detailed description. It is intended that all such additional systems, devices, methods, features and advantages be included within this description, be within the scope of the subject matter described herein, and be protected by the accompanying claims. In no way should the features of the example embodiments be construed as limiting the appended claims, absent express recitation of those features in the claims.

BRIEF DESCRIPTION OF THE FIGURES

The details of the subject matter set forth herein, both as to its structure and operation, may be apparent by study of the accompanying figures, in which like reference numerals refer to like parts. The components in the figures are not necessarily to scale, emphasis instead being placed upon illustrating the principles of the subject matter. Moreover, all illustrations are intended to convey concepts, where relative sizes, shapes and other detailed attributes may be illustrated schematically rather than literally or precisely.

FIG. 14 is a side view depicting an example embodiment of tubing for use in the construction of a catheter.

FIGS. 15A-B are diagrams depicting an example embodiment of additional manufacturing steps for an interior of the device including bonding a proximal and distal tube to create a third tube with an inflation port.

DETAILED DESCRIPTION

Before the present subject matter is described in detail, it is to be understood that this disclosure is not limited to the particular embodiments described, as such may, of course, vary. It is also to be understood that the terminology used herein is for the purpose of describing particular embodiments only, and is not intended to be limiting, since the scope of the present disclosure will be limited only by the appended claims.

As used herein and in the appended claims, the singular forms "a", "an", and "the" include plural referents unless the context clearly dictates otherwise.

The publications discussed herein are provided solely for their disclosure prior to the filing date of the present application. Nothing herein is to be construed as an admission that the present disclosure is not entitled to antedate such publication by virtue of prior disclosure. Further, the dates of publication provided may be different from the actual publication dates which may need to be independently confirmed.

It should be noted that all features, elements, components, functions, and steps described with respect to any embodiment provided herein are intended to be freely combinable and substitutable with those from any other embodiment. If a certain feature, element, component, function, or step is described with respect to only one embodiment, then it should be understood that that feature, element, component, function, or step can be used with every other embodiment described herein unless explicitly stated otherwise. This paragraph therefore serves as antecedent basis and written support for the introduction of claims, at any time, that combine features, elements, components, functions, and steps from different embodiments, or that substitute features, elements, components, functions, and steps from one embodiment with those of another, even if the following description does not explicitly state, in a particular instance, that such combinations or substitutions are possible. It is explicitly acknowledged that express recitation of every possible combination and substitution is overly burdensome, especially given that the permissibility of each and every such combination and substitution will be readily recognized by those of ordinary skill in the art.

Figure 1:
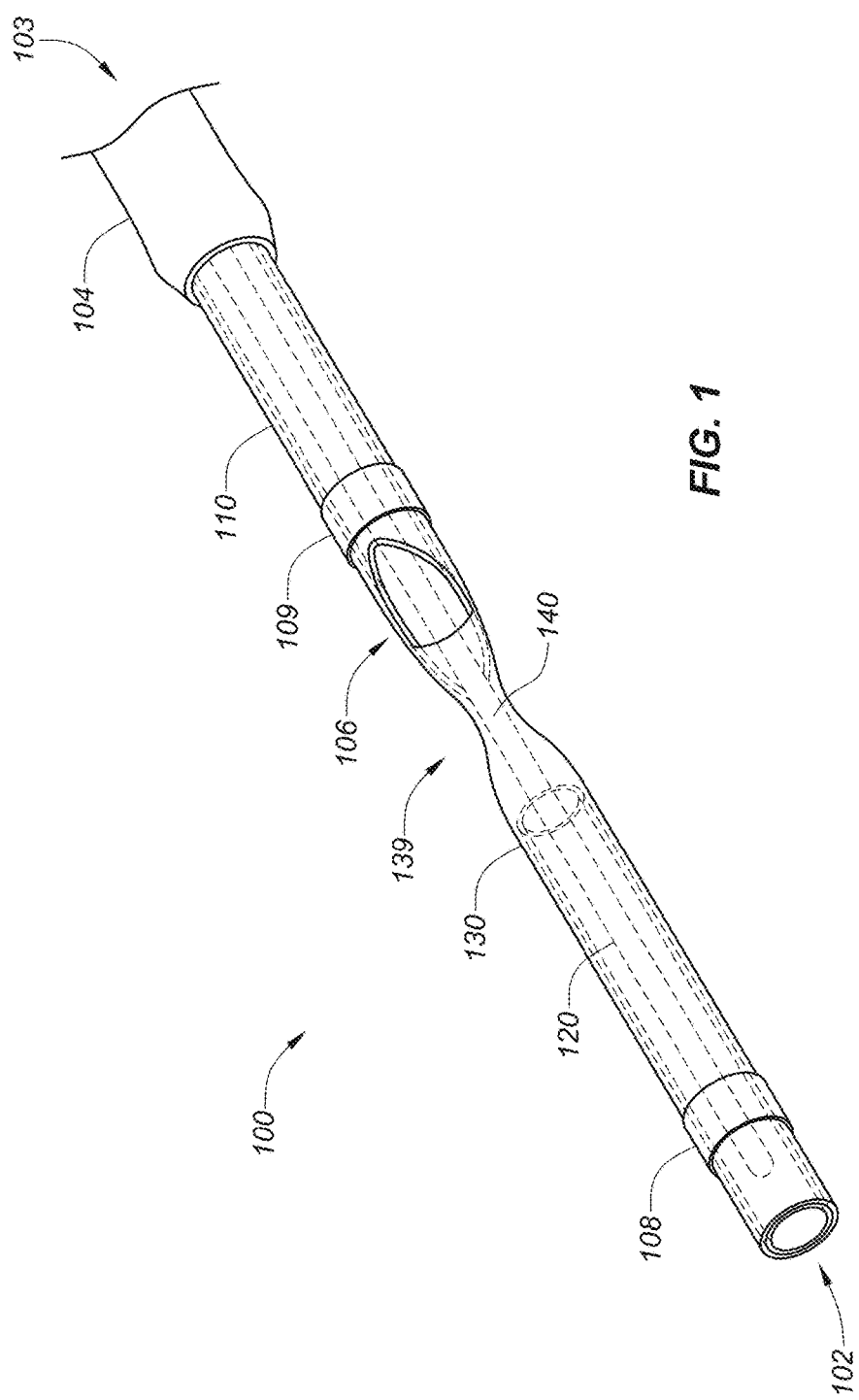
FIG. 1 is a perspective view depicting an example embodiment of the catheter device without an expandable member.
Figure 2:
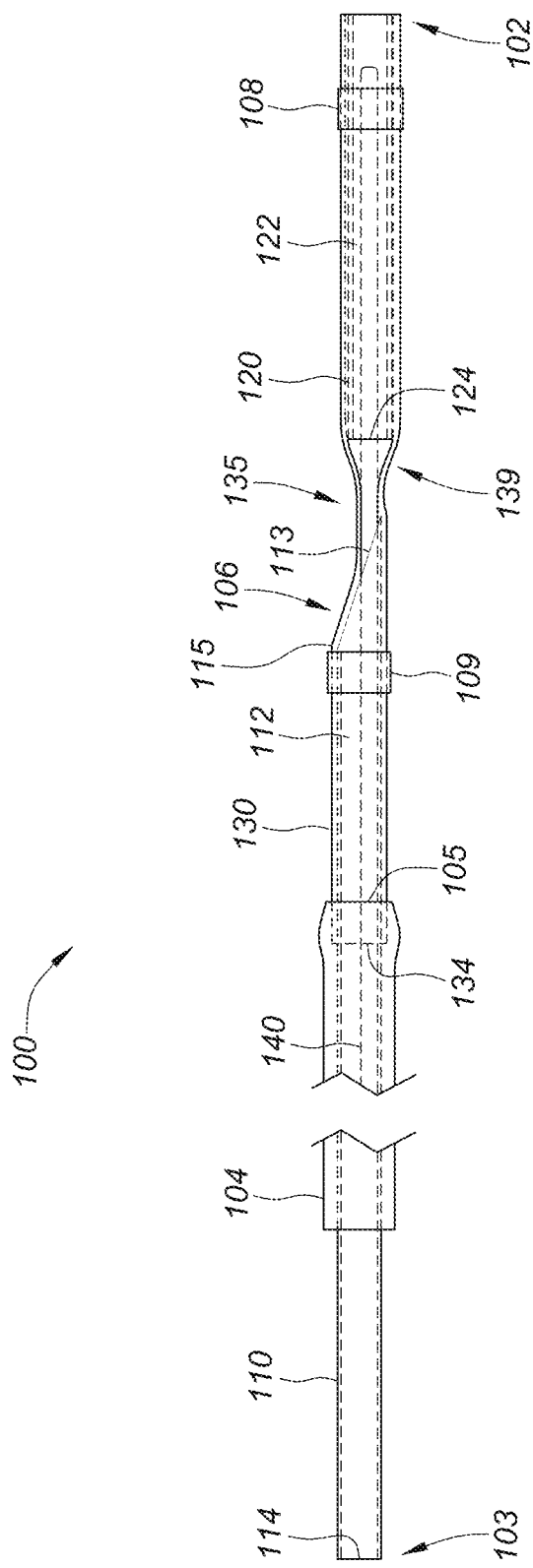
FIG. 2 is a partial cross-sectional side view depicting an example embodiment of the catheter device without the expandable member.
Figure 3:
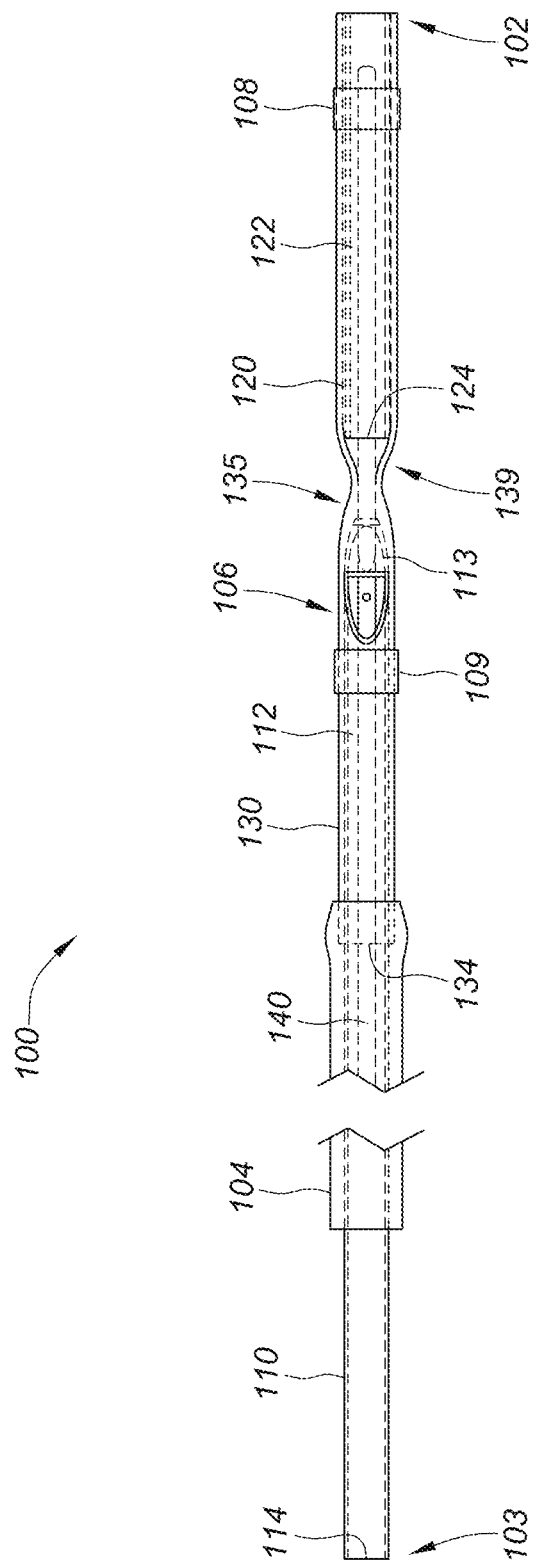
FIG. 3 is a partial cross-sectional top view depicting an example embodiment of the catheter device without the expandable member.
Figure 4:
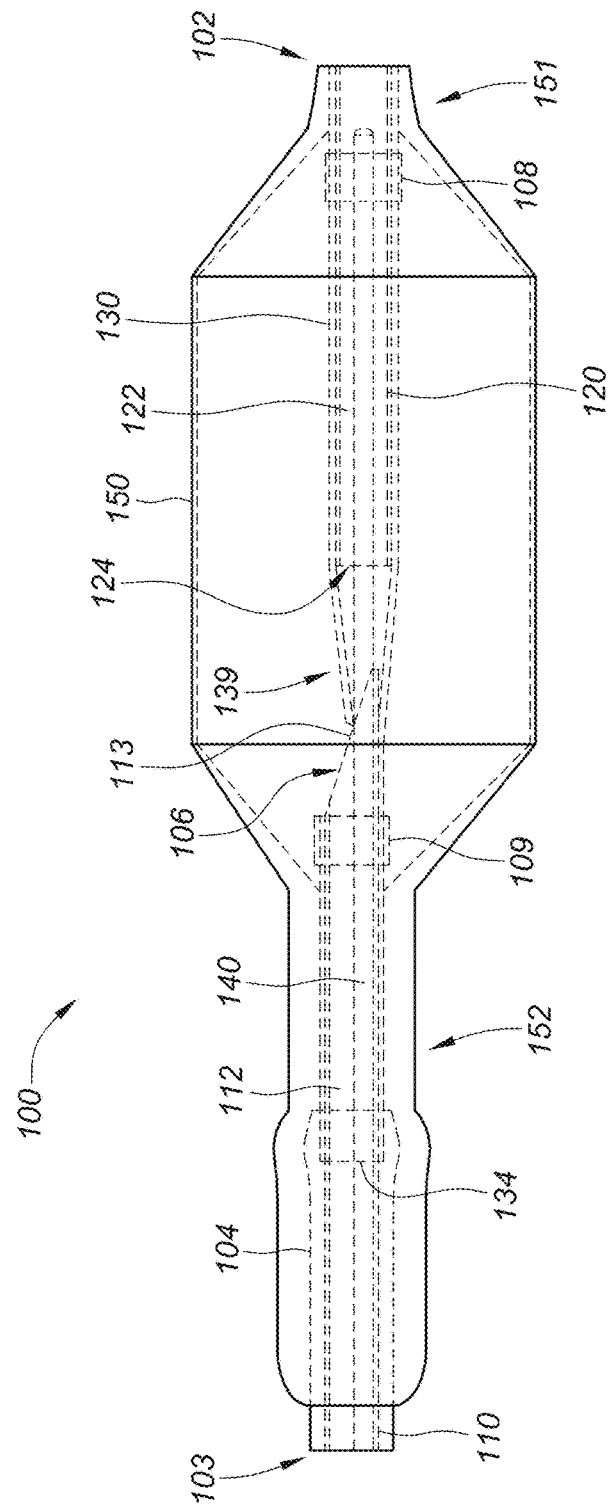
FIG. 4 is enlarged partial cross-sectional side view depicting an example embodiment of the catheter device with the expandable member in an inflated configuration.
Figure 5:
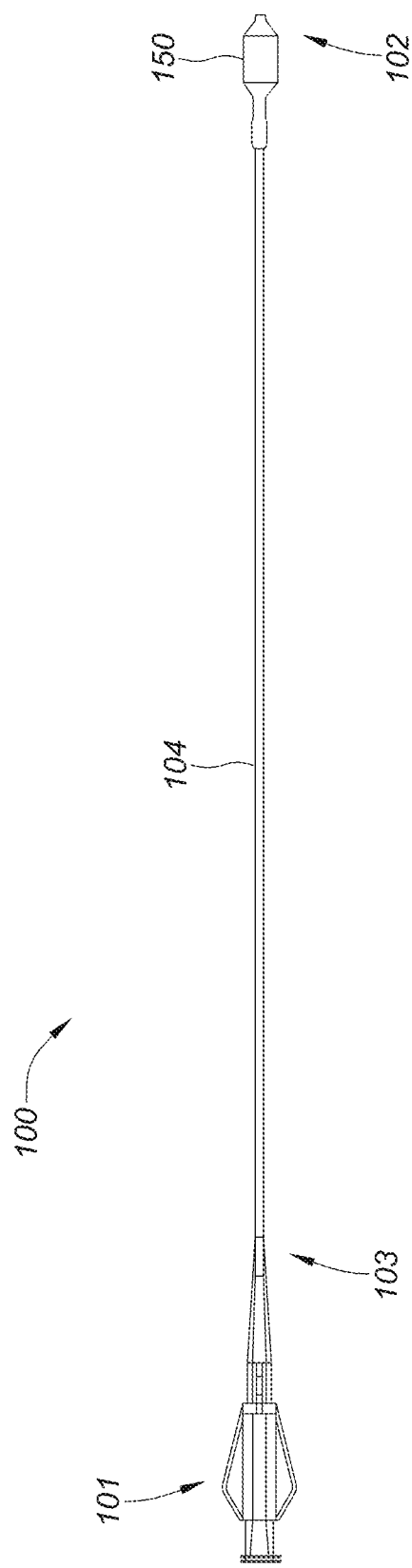
FIG. 5 is a side view depicting an example embodiment of the full catheter device.
Figure 6:
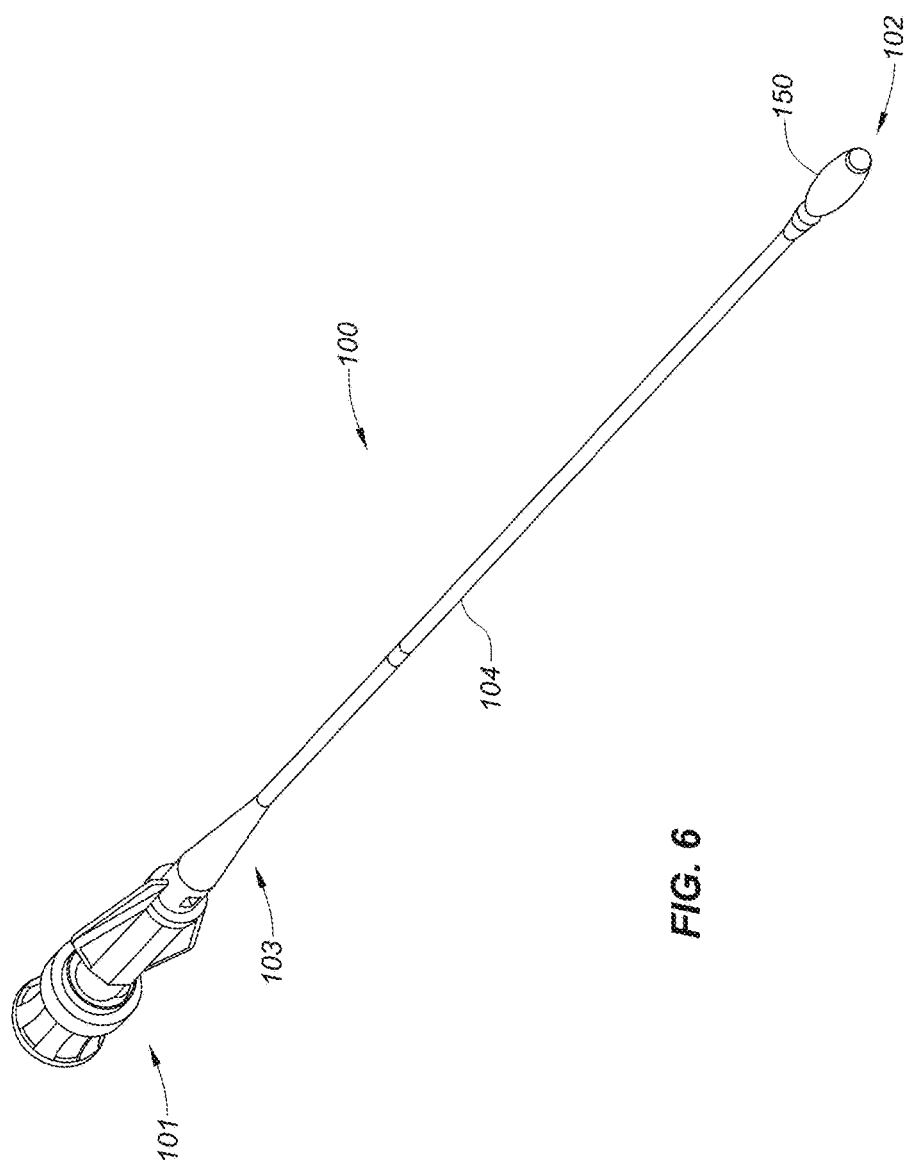
FIG. 6 is a perspective view of the full catheter device.

FIGS. 1-6 are various views depicting an example embodiment of a catheter device 100 for use in compacting cancellous bone. Here, catheter device 100 has a distal end 102 and a proximal end 103. FIGS. 1, 2, and 3 are a perspective view, partial cross-sectional side view, and partial cross-sectional top view, respectively, of catheter device 100 in an intermediate stage of construction prior to attachment of an expandable member 150. FIG. 4 is a partial cross-sectional side view depicting catheter 100 in a late or final stage of construction after attachment of expandable member 150. FIGS. 5-6 are side and perspective views, respectfully, of the entire catheter 100 with a proximal controller 101, which allows the operation and manipulation of catheter device 100 and includes an inflation inlet and deflation outlet for expandable member 150.

Catheter device 100 includes, in part, a first tubular member (or tube) 110 located generally proximally, a second tubular member (or tube) 120 located distal to and separated from first tubular member 110, and a third tubular member (or tube) 130 within which first tube 110 and second tube 120 are located.

In this embodiment, first tube 110 has an inner lumen 112 and an open beveled end 113. Third tube 130 has an opening in its sidewall over open beveled end 113 such that an inflation port 106 is formed through which an inflation medium (e.g., saline) can pass from inner lumen 112 of first tube 110 to inflate expandable member 150. The opening in beveled end 113 is shown as having an oval shape in FIG. 3, although any profile shape can be used.

A proximal end 114 of first tube 110 extends proximally to (or constitutes) proximal end 103 of catheter 100. A proximal end 134 of third tube 130 is positioned at an intermediate location along the catheter shaft. An outer sheath 104 can extend along the majority or all of first tube 110 and can cover proximal end 134 of third tube 130 such that the outer sheath's distal end 105 is between third tube proximal end 134 and inflation port 106. In alternative embodiments, third tube proximal end 134 can extend to proximal end 103 of catheter 100 with first tube 110, or instead of first tube 110 if proximal end 114 terminates at an intermediate location.

The terminus of distal end 113 of first tube 110 is separated from the terminus of a proximal end 124 of second tube 120 such that, of the three tubes 110, 120, and 130, only third tube 130 extends therebetween. As will be described later, e.g., with respect to FIGS. 11-15, in some embodiments, third tube 130 is formed by bonding a proximal tube with a distal tube to form a single continuous tube. In other embodiments, third tube 130 is formed from a single continuous member without coupling multiple tubes together. Third tube 130 can be formed from an elastic material, such as pellethane and the like, that can stretch and contract to vary the distance between first tube 110 and second tube 120. This region of third tube 130 is referred to herein as variable length section 139. In the embodiment of FIGS. 1-4 section 139 forms a "neck" and has a reduced diameter as compared to tubes 110 and 120 and the regions of tube 130 located both distal and proximal to section 139. In FIGS. 2-3, variable length section 139 is distal and adjacent to a bond 135 between third tube 130 and mandrel 140. This bonded area 135 does not change length, although the tapered variable length section 139 does. In FIG. 4, bonded area 135 is omitted. As is discussed in more detail with respect to FIGS. 15A-B, bonded area 135 can limit the size of variable length section 139 and thus the amount by which catheter 100 can change length.

Variable length section 139, among other functions, allows expandable member 150 to more closely fit against the catheter shaft during withdrawal from a vertebral body. Variable length section 139 also allows distal end of catheter 102 to extend in a longitudinal direction such that expandable member 150 will not extend past distal end of catheter 102. Expandable member 150 can be configured as a balloon (as shown in FIG. 4) that is coupled to third tube 130 at a distal coupling location 151 and a proximal coupling location 152. Distal coupling location 151 can be at the distal end of second tube 120 and proximal coupling location 152 begins (when viewing distal to proximal) at first tube 110 and can extend any additional distance proximally. Here proximal coupling location 152 extends proximally past proximal end 134 of first tube 110. In many embodiments proximal coupling location 152 can extend proximally from a proximal terminus 115 of open beveled end 113 (i.e., the proximal terminus of the beveled face).

Any number of radiopaque (RO) markers can be added to catheter 100 to aid in visualization during the medical procedure. In this embodiment, a distal RO marker 108 is located just proximal to distal coupling section 151. A proximal RO marker 109 is located just distal to proximal coupling location 152. RO markers 108 and 109 can be in the form of bands wrapped about the exterior of third tube 130 and can be affixed with adhesive. Other configurations and methods of attachment for RO markers 108 and 109 are known in the art and can be used as well. Placement in these locations can assist the medical professional in locating the limits of expandable member 150 prior to inflation to create the interior cavity in the cancellous bone.

A mandrel 140 (which can also be referred to as a stylet or stiffening member) is received within the lumen 122 of second tube 120, passes through beveled end 113 and into first lumen 112. The width (or diameter) of mandrel 140 is less than that of first lumen 112 to allow the inflation medium to pass through lumen 112 and port 106. The width (or diameter) of mandrel 140 is also less than that of second tube lumen 122 to allow second tube 120 to slide back and forth along mandrel 140 during inflation and deflation of member 150. In this respect, mandrel 140 serves as a guide that maintains second tube 120 in the proper alignment throughout movement.

First tube 110 and second tube 120 can be formed from a metal or polymer that is of sufficient rigidity to withstand the pressures created during inflation of expandable member 150. First tube 110 and second tube 120 can be formed from the same or different materials. In some embodiments, first tube 110 and second tube 120 are formed from Pebax 70D. In other embodiments, first tube 110 is stainless steel and second tube 120 is Pebax 70D. Other variations are possible. Because third tube 130 is formed from an elastic material, in most embodiments, third tube 130 is generally not capable of maintaining second tube 120 in position with respect to first tube 110. Therefore, in most embodiments mandrel 140 can also be formed of a rigid metal (e.g., stainless steel, nitinol, etc.) or polymer that is stiff enough to hold second tube 120 in position without substantial lateral deflection with respect to first tube 110. Mandrel 140 can be formed from a metal or polymer with the same or greater stiffness than the material(s) of first tube 110 and/or second tube 120.

In many embodiments expandable member 150 has elastic properties which allow it to stretchably expand and contract. In some embodiments, expandable member 150 may be made of thermoplastic polyurethane (TPU). Expandable member 150 can also be formed from an inelastic or substantially inelastic balloon that resists significant stretching, as are known in the art. Also, expandable member 150 may be made of a single component/layer or multiple components/layers which allow it to expand and contract as desired for the particular medical procedure.

Figure 7:
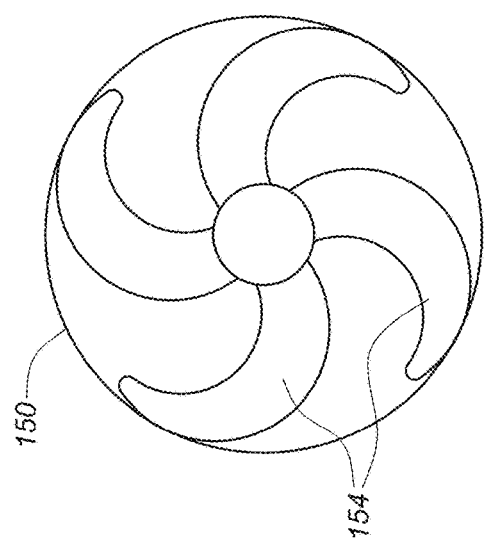
FIG. 7 is a cross section depicting an example embodiment of the catheter device with an expandable member in an uninflated configuration.

Expandable member 150 is operable to change configurations from a collapsed first configuration to an inflated second configuration. An example of an inflated second configuration can be seen in FIG. 4. The collapsed first configuration is ideal for the introduction of catheter device 100 into a vertebral body of the patient because expandable member 150 is in its most compact form. FIG. 7 is an end-on view depicting an example embodiment of expandable member 150 in a collapsed first configuration with four curved pleats or folds 154 that allow for compact delivery. In an example bone compaction procedure, a hole is first created (e.g., drilled) in the cortical layer surrounding the cancellous bone. Catheter 100, with expandable member 150 not inflated and folded against the catheter shaft, is then inserted (e.g., from a cannula) through the hole in the cortical layer and into the interior region where the cancellous bone is located.

Expandable member 150 can then be filled with an inflation medium in order to reach the inflated second configuration of FIG. 4. Pleats 154 (FIG. 7) will unravel or unfold when subjected to interior pressure due to outflow of the inflation medium from port 106 and into the interior space of expandable member 150. A high degree of force can be generated by expandable member 150 to allow it to push and compact the cancellous bone. Expandable member 150 should therefore be of sufficient strength and durability to compact cancellous bone without rupturing during inflation. This process is described in relation to FIGS. 22A-26, described further below.

When filled with inflation medium (e.g., saline) expandable member 150 can expand in both a longitudinal direction (to increase length) and a radial direction (to increase circumference or perimeter). Expansion in a longitudinal direction causes third tube 130 to stretch while second tube 120 is advanced distally. For deflation, the medium may be removed from expandable member 150 by reversing the flow of the inflation medium after the conclusion of the cancellous bone compacting procedure such that the inflation medium passes back through port 106 and into first tube lumen 112. In doing so, expandable member 150 will deflate from the inflated second configuration to a deflated third configuration. The deflated third configuration is also accompanied by contraction of third tube 130 in variable length section 139 from its expanded state in the inflated second configuration to a configuration similar to the first configuration. Second tube 120 moves proximally as well towards the position of the first configuration (closer to beveled end 113 of first tube 110).

The removal or extraction of catheter device 100 from the cancellous bone area (e.g., back into a cannula) occurs through the same opening in the cortical bone through which it was introduced. However, it is difficult to return expandable member 150 to a folded state resembling that prior to inflation (e.g., that of FIG. 7). When using some conventional compaction catheters with a narrow opening in the cortical bone, there is minimal room for withdrawal of catheter 100 and, as a result, expandable member 150 may begin to bunch up within the vertebral cavity adjacent the cortical opening, which can inhibit its removal from the vertebral body. This undesirable result can be avoided in certain embodiments by variable length section 139. If expandable member 150 begins to bunch up as catheter 100 is withdrawn then expandable member 150 will pull on catheter 100 and cause variable length section 139 to advantageously elongate. The elongation will allow for longitudinal elongation (or extension or expansion) of catheter 100, which accordingly allows expandable member 150 to reside more closely against the catheter shaft and facilitate withdrawal through the cortical opening.

Figure 8:
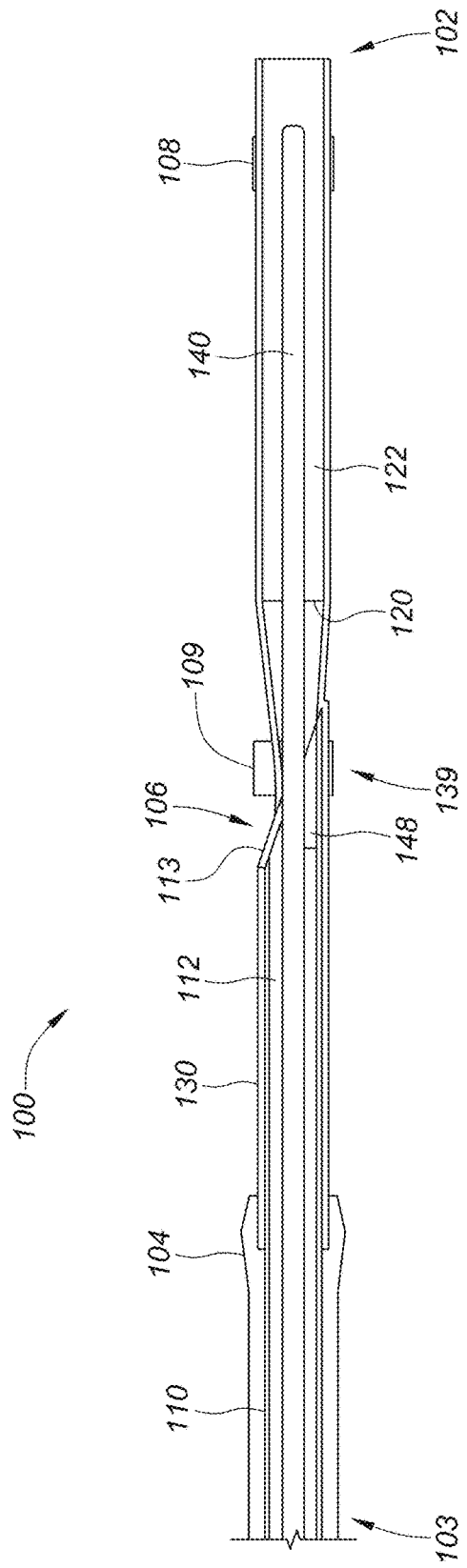
FIG. 8 is a side view depicting an example embodiment of the catheter device with a shim spacer.
Figure 9:
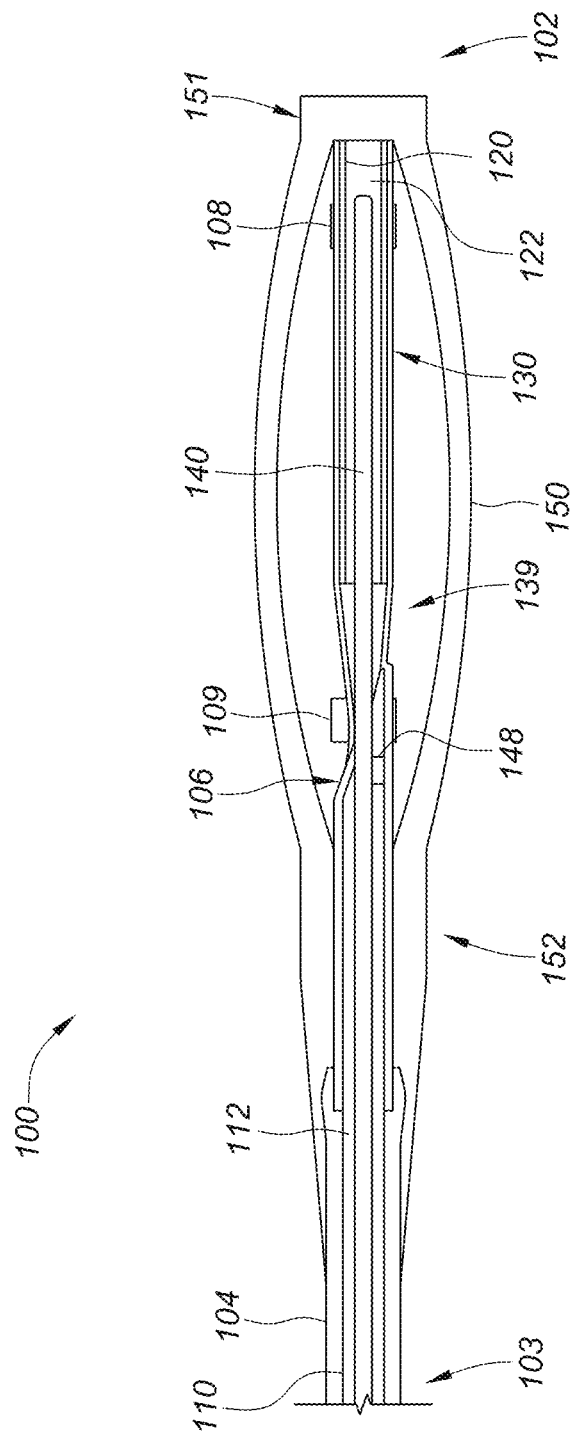
FIG. 9 is a side view depicting an example embodiment of the catheter device with a shim spacer and the expandable member in an inflated configuration.

FIGS. 8-9 are partial cross-sectional side views of another example embodiment of catheter 100, without and with a partially inflated expandable member 150, respectively. In this embodiment, catheter 100 includes a spacer or shim 148 near open beveled end 113. Shim 148 can be configured to provide interior support, alignment assistance, or spacing between components. For example, the neck in section 139 can cause mandrel 140 to be positioned against the interior sidewall of lumen 122 opposite to and facing the opening in beveled end 113, which in turn can allow the distal section of catheter 100 having second tube 120 to align around mandrel 140 in a position that is displaced relative to first tube 100. Shim 148 can adjust the position of mandrel 140 so that a center longitudinal axis of mandrel 140 is aligned with a center longitudinal axis of first tube 110, and thus any alignment of second tube 120 around mandrel 140 will also align with first tube 110.

The embodiment of FIGS. 8-9 also differs from that of FIGS. 1-4 in the position of proximal RO marker 109, which is now located directly over variable length section 139 adjacent and distal to inflation port 106.

Also provided herein are example embodiments of methods of manufacturing catheter device 100. These methods typically involve a number of steps that are described below. Those of ordinary skill in the art will recognize from this description that the order in which these steps can be carried out can vary from the order described here.

Figure 10:
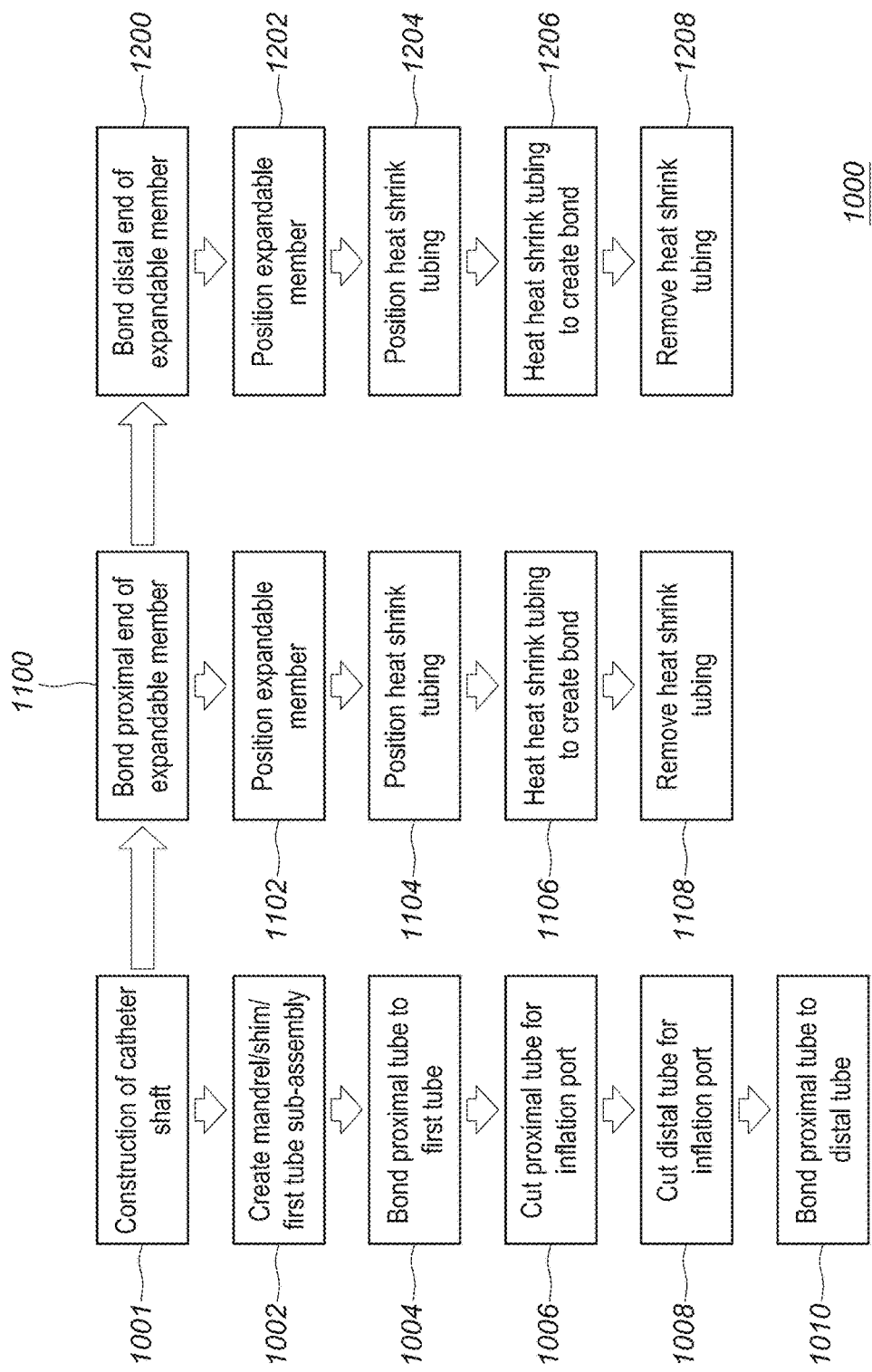
FIG. 10 is a flow diagram depicting an example embodiment of a manufacturing process.

FIG. 10 is a flowchart depicting an example embodiment of a manufacturing process 1000. In general, manufacturing process 1000 will include the general steps of construction of the catheter shaft at 1001, then bonding of the proximal end of an expandable member at 1100, and then bonding of the distal end of an expandable member at 1200. Each of these general steps can include a number of sub-steps (e.g., 1002-1010, 1102-1108, and 1202-1208). These sub-steps can be exchanged, omitted, expanded, or repeated as necessary. Likewise steps 1100 and 1200 can be performed in the reverse order. The steps and sub-steps described above will now be described in greater detail with specific example embodiments shown in FIGS. 11-21.

Figure 11A:
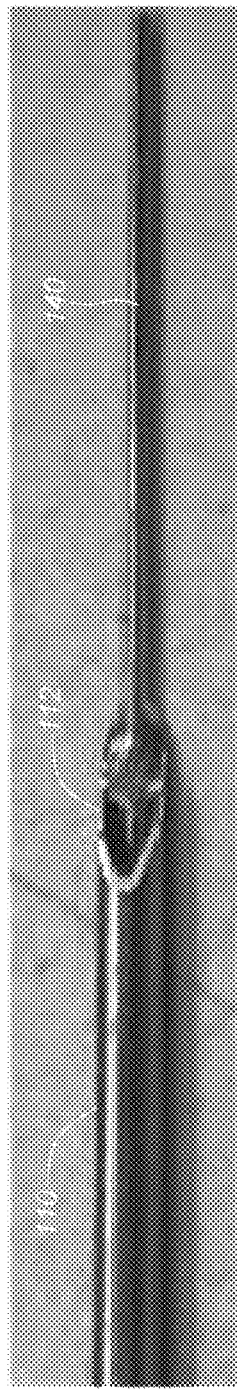
FIGS. 11A-11B are diagrams depicting an example embodiment of manufacturing steps for an interior of the device.

A first step in the manufacturing of catheter shaft 1001 can be sub-step 1002 where an optional shim spacer 148 (seen in FIGS. 8, 9) is assembled with first tube 110 and mandrel 140. As depicted in FIG. 11A, mandrel 140 can first be guided into first tube lumen 112 and shim spacer 148 (obscured) can subsequently be placed in between an interior surface of first tube 110 and mandrel 140. In embodiments where shim spacer 148, mandrel 140 and first tube 110 are all metal, the components can be resistance welded or soldered together. In embodiments where one or more of shim spacer 148, mandrel 140 and first tube 110 are not metal, one or more adhesive materials can be used to secure positioning of the components. In some embodiments shim spacer 148 is cut from another piece of tubing using a laser.

Once a secured assembly of first tube 110, shim spacer 148, and mandrel 140 is prepared, then a proximal tube 131 can be bonded to first tube 110 (sub-step 1004 of FIG. 10) by first sliding it over and around the assembly. Alignment of, for example, a 14 mm long proximal tube 131 can be achieved by positioning the proximal 12 mm length of proximal tube 131 around first tube 110 while the distal 2 mm length can be positioned around the mandrel 140. In other embodiments different positions can be used.

Figure 11B:
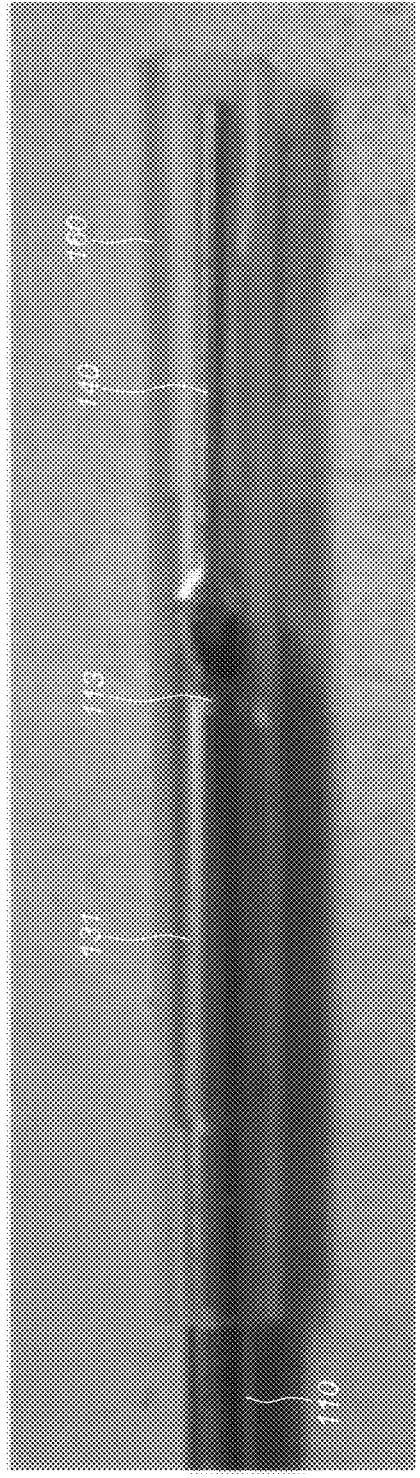

FIG. 11B shows an example embodiment of a heat shrink tube 160 positioned around the secured assembly of first tube 110, shim spacer 148, and mandrel 140 along with proximal tube 131 in the described position. Once the heat shrink tube 160 is in place it can be heated such that it will cause proximal tube 131 to bond with first tube 110. In an example embodiment heat can be applied from the proximal end of heat shrink tube 160 while rotating the assembly about its longitudinal axis. The heat is moved distally until reaching the proximal terminus of open beveled end 113. Here, heat is not applied to the tubing over open beveled end 113. Heat shrink tube 160 can then be removed by peeling it from the assembly. The assembly can then be examined to ensure that proximal tube 131 is uniformly bonded with first tube 110.

Figure 12A:
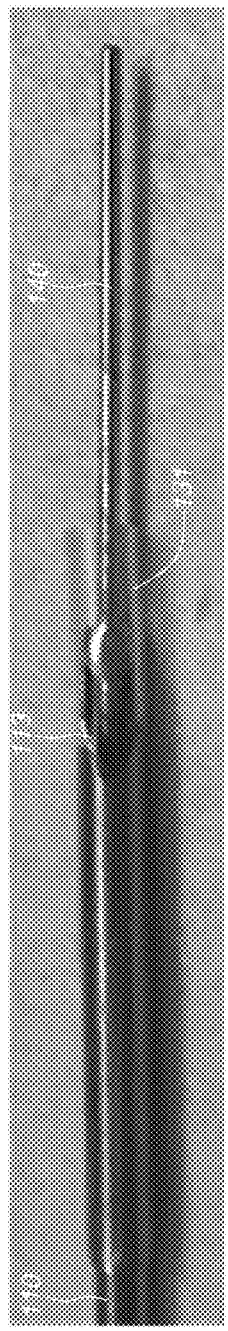
FIGS. 12A-12C are diagrams depicting an example embodiment of subsequent manufacturing steps for the interior of the device including creation of a first side of an inflation port for the interior of an expandable member.

FIG. 12A is a top view showing an example embodiment of the assembly with heat shrink tube 160 removed. At this stage proximal tube 131 is not yet bonded at its distal end. Proximal tube 131 can be cut such that an opening over open beveled end 113 is created (sub-step 1006 of FIG. 10). The opening can be the same size as open beveled end 113 or can have a different size. The assembly can be examined to ensure that the cut portion of proximal tube 131 has left an adequate opening over open beveled end 113.

Figure 12B:
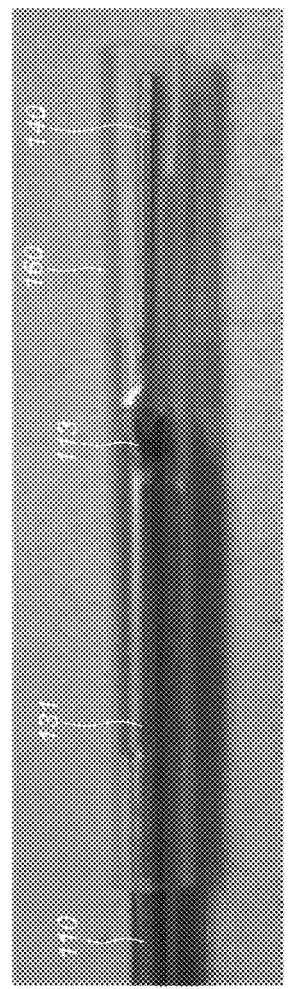
Figure 12C:
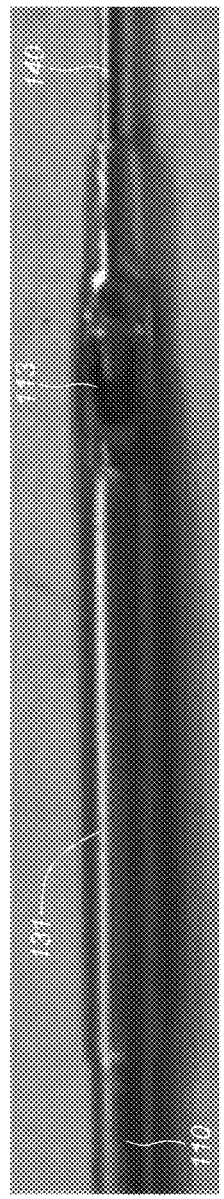

FIG. 12B depicts the assembly with another heat shrink tube 160 around proximal tube 131 after proximal tube 131 has been cut. Heat shrink tubing 160 can then be heated in a manner similar to that already described, starting at the proximal end and moving distally while rotating about a longitudinal axis of the assembly. In this step, the distal end of proximal tube 131 is heated such that it bonds to mandrel 140. Heat shrink tube 160 can then be removed, for example, by peeling it away from the assembly. After removal of heat shrink tube 160, the assembly can be examined to ensure that proximal tube 131 is fully and uniformly bonded with guiding mandrel 140. If imperfections such as "cloudiness" exist in the bond then another heat shrink tube 160 can be positioned and heated. The process can be repeated as necessary to create the uniform bond depicted in FIG. 12C.

Figure 13A:
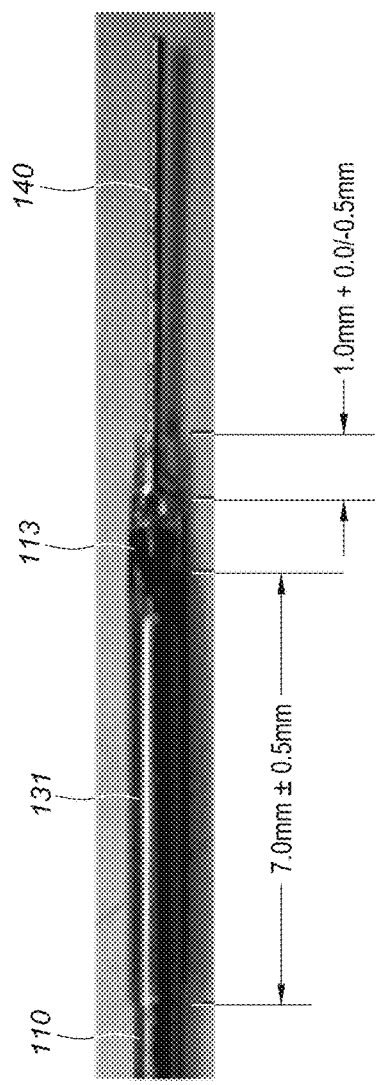
FIGS. 13A-13B are diagrams depicting an example embodiment of additional manufacturing steps for the interior of the device including trimming a portion of a proximal tube.
Figure 13B:
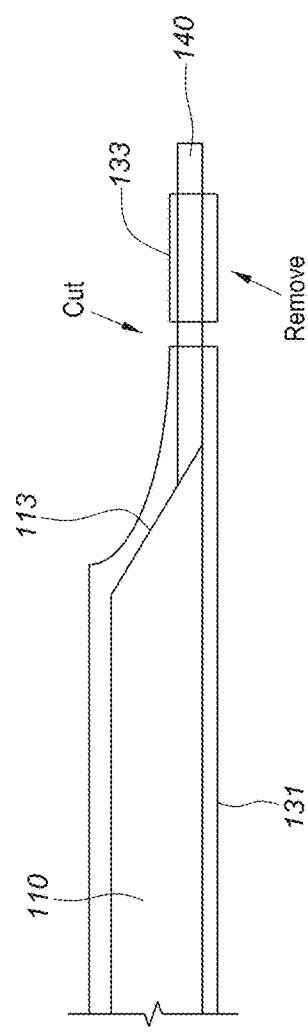

FIGS. 13A-B show an example embodiment of preparing proximal tube 131 for bonding with distal tube 132 (shown in later figures). In the example embodiment a 1.0 mm+/−0.5 mm length of proximal tube 131 can be measured from the distal end of first tube 110 distally along mandrel 140. At that location proximal tube 131 can be cut and material 133 located distal to the cut can be removed. A check may be made of proximal tube 131 from the opening over beveled end 113 to the proximal end of proximal tube 131 to determine whether it is within a desired range, for example 7.0 mm+/−0.5 mm.

Distal tube 132 can now be prepared for bonding to proximal tube 131 by cutting or otherwise forming an arc shape (e.g., a crescent) in its proximal end as seen in FIG. 14 (sub-step 1008 of FIG. 10).

FIGS. 15A-B show an example embodiment of the creation of a bonded area 135 between proximal tube 131 and distal tube 132 to create third tube 130 (sub-step 1010 of FIG. 10). Initially distal tube 132 can be slid around mandrel 140 such that it overlaps a portion of proximal tube 131 and the cut at the distal end of proximal tube 131 aligns at least partially with the cut at the proximal end of distal tube 132, creating an inflation port 106 aligned at least partially over open beveled end 113. A heat shrink tube 160 (not shown)

can be placed over the assembly and heated such that proximal tube 131 and distal tube 132 are heated and bond at bonded area 135. The bonded area 135 (or "bond") can include a bond between tubes 131, 132 and underlying mandrel 140. Heating can begin at distal tube 132, for example at a location 1 mm distal to the terminus of proximal terminus 115 and move proximally. In some embodiments, heating does not occur past the distal end of proximal tube 131. This process can be repeated as necessary to create a seamless bond, by which third tube 130 is fabricated and by which third tube 130 is bonded to mandrel 140. The bond 135 (see also FIG. 2) of third tube 130 to mandrel 140 assists in limiting the degree by which variable length section 139 will stretch.

A marker band 109 in some embodiments can be placed in position over the welded portion of mandrel 140 and first tube 110 such that it does not cover or otherwise substantially obstruct inflation port 106.

Alternative fixation techniques can be used to create bonded area 135 such as adhesives, and others, depending on the type of material used in proximal tube 131 and distal tube 132 and the inherent physical properties of each.

Figure 16:
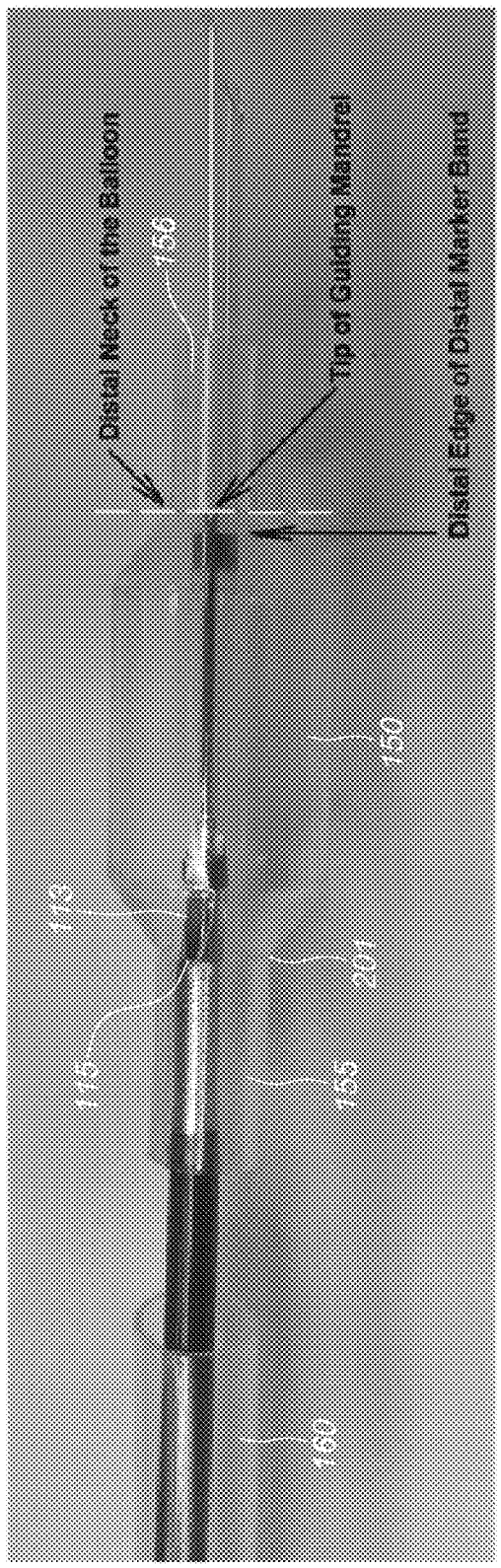
FIGS. 16-21 are side views depicting additional example embodiments of the catheter device during various manufacturing steps.

Turning now to general steps 1100 and 1200 of FIG. 10, expandable member 150 can have a proximal leg 155 and a distal leg 156 such that the legs can be bonded and/or secured to the catheter shaft (see FIG. 16). In some embodiments proximal leg 155 and distal leg 156 can be trimmed to desired dimensions such that they are square cuts, perpendicular to a longitudinal axis running lengthwise through the center of expandable member 150 and creating a circular cross sectional profile. Proximal leg 155 can be trimmed, for example about 7 mm in length, and distal leg 156 can be trimmed, for example, about 5 mm in length. Expandable member 150 in the example embodiment has tapered portions at both its proximal and distal ends which taper from a larger cross-sectional area to the smaller cross-sectional area of proximal leg 155 and distal leg 156 respectively, and the middle section can have a substantially uniform cross-sectional area.

FIG. 16 is a perspective view depicting a subsequent step in manufacturing. Here, expandable member 150 with proximal leg 155 and distal leg 156 has been slid over third tube 130 until the distal transition 201 of proximal leg 155 is approximately aligned with the proximal terminus 115 of open beveled end 113 such that inflation port 106 (not labeled) is left unobstructed (sub-step 1102 of FIG. 10). Heat shrink tube 160 can be advanced distally over the catheter shaft such that it slides over proximal leg 155 to its distal transition 201 (sub-step 1104 of FIG. 10).

Figure 17:
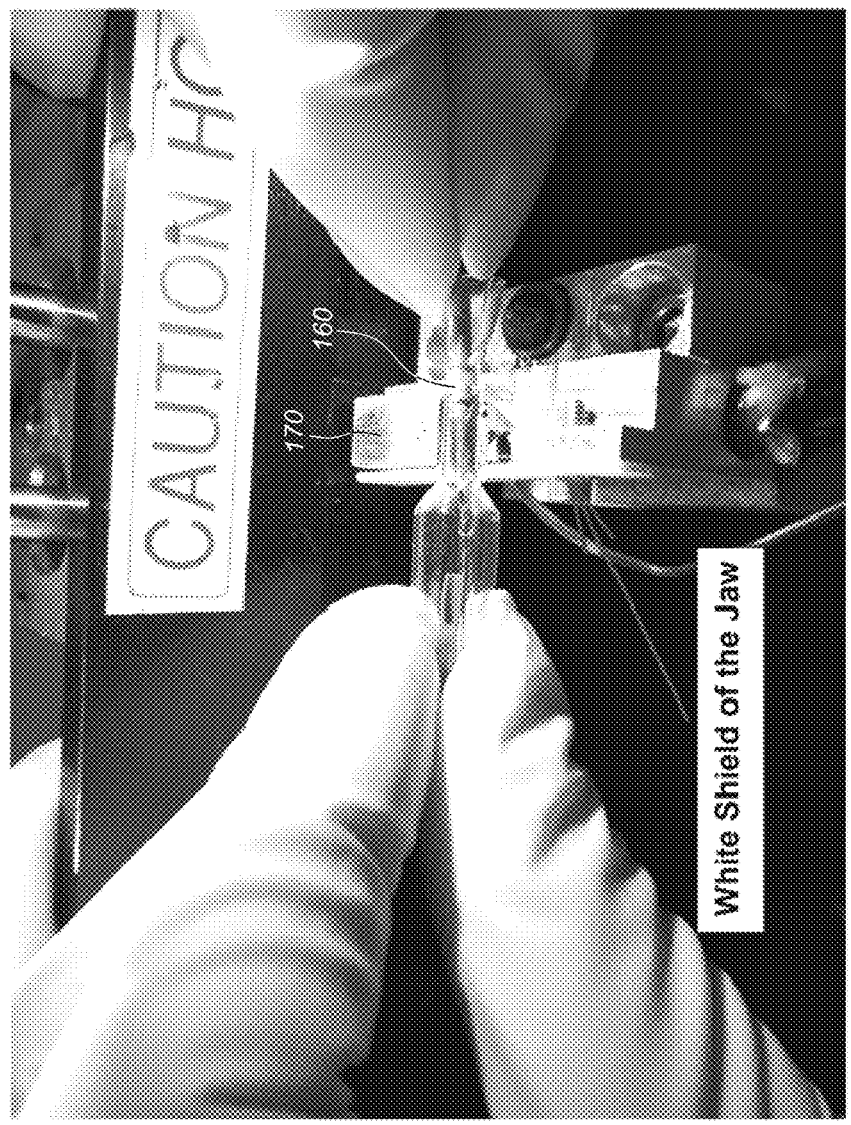

FIG. 17 shows an example embodiment of an initial proximal leg bonding process to bond proximal leg 155 to third tube 130, and in some embodiments first tube 110 and sheath 104. After the heat shrink tube 160 is placed over proximal leg 155, heat shrink tube 160 and proximal leg 155 assembly can be positioned such that a cross section of proximal leg 155 is perpendicular with a longitudinal axis running through the center of expandable member 150 and is parallel and aligned with a heating element 170. Heating of heating element 170 can cause heat shrink tube 160 to shrink and transfer heat to proximal leg 155 and cause it to fuse and/or bond to third tube 130 (sub-step 1106 of FIG. 10) at proximal coupling location 152. When the heating process is finished, the operator can remove heat shrink tube 160 by peeling it from proximal leg 155 (sub-step 1108 of FIG. 10).

Figure 18:
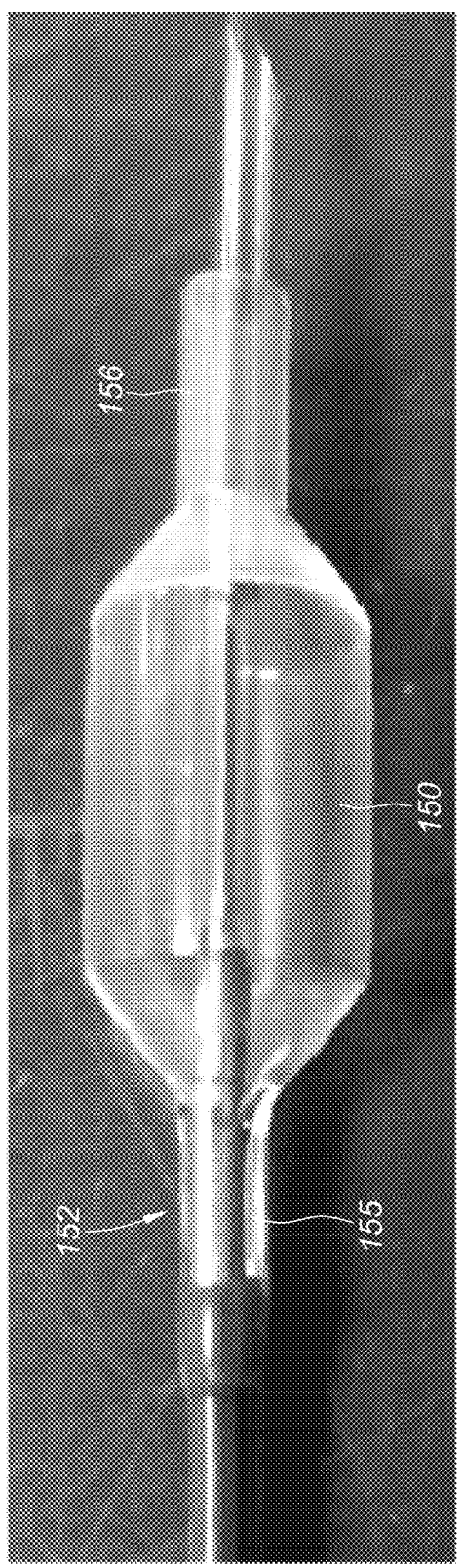
Figure 19:
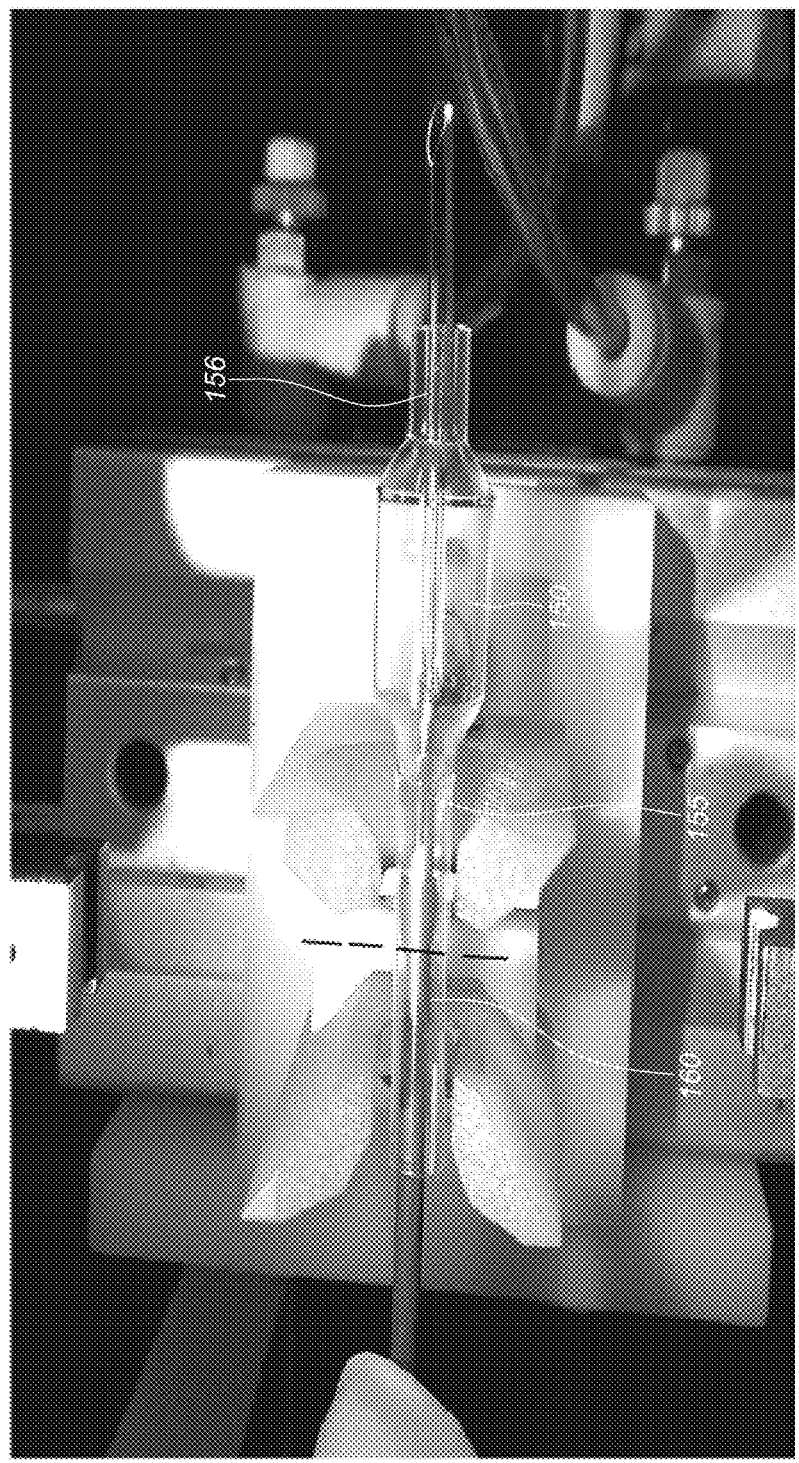

FIG. 18 shows an example embodiment of the assembly after a first proximal leg bonding process. In order to reduce the width or diameter of the proximal leg bond and/or also to improve the taper of the bond, a second proximal leg bonding process may be applied by repeating the same steps with a smaller or similarly sized heat shrink tube. This is shown in FIG. 19. The process can be iteratively repeated with similarly sized or sequentially smaller diameter heat shrink tubes, or any combination thereof. The reduced bond diameter and improved taper of proximal leg 155 can offer a cross-sectional profile that is less intrusive in medical procedures.

Figure 20:
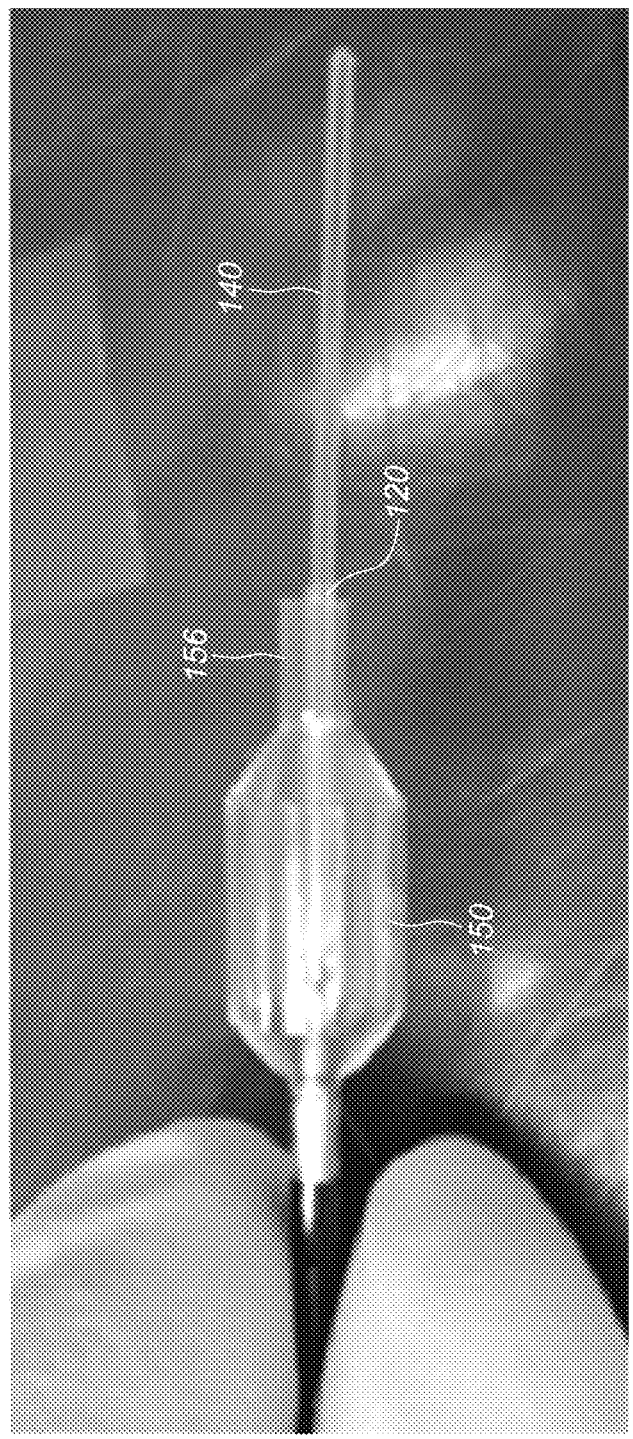

FIG. 20 is a side view depicting a next step in the manufacturing process where second tube 120 has been inserted into third tube 130 such that mandrel 140 is situated in second tube inner lumen 122 (not labeled). In many embodiments second tube 120 can be advanced along mandrel 140 in a proximal direction until reaching the location where third tube 130 is bonded to mandrel 140. The resulting assembly can then be put through a distal leg bonding process. Mandrel 140 can be trimmed to a specified length if necessary at various steps herein.

Figure 21:
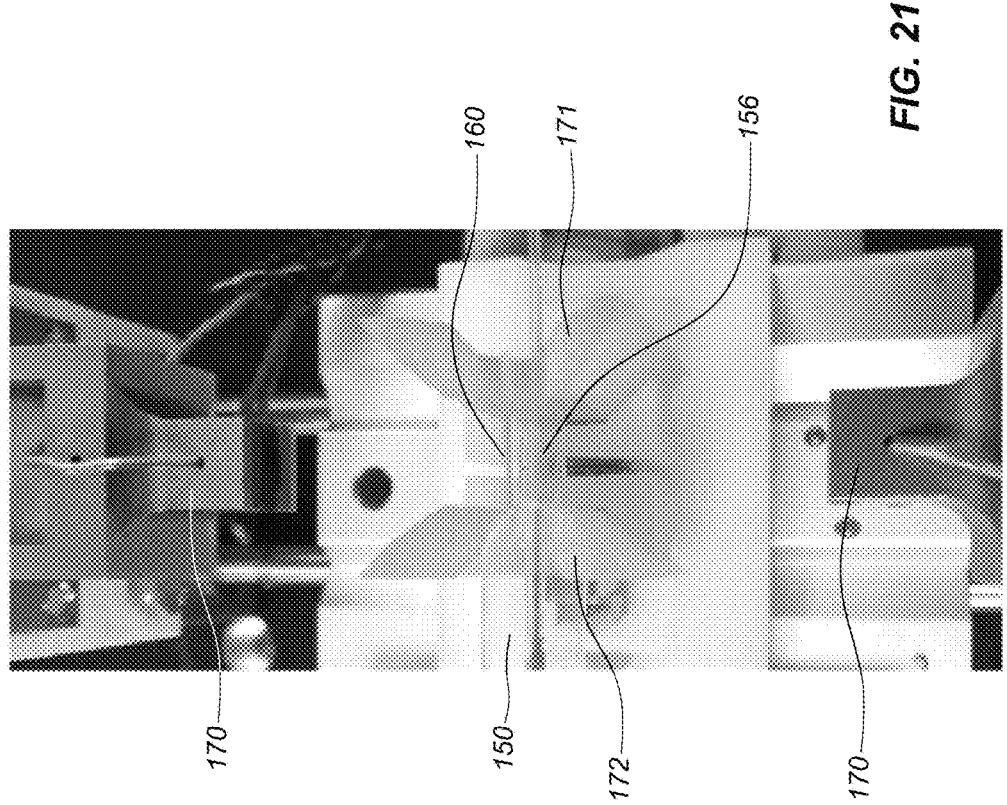
Figure 22B:
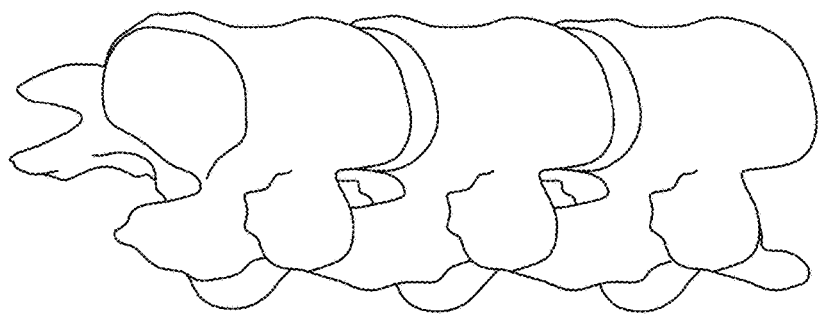
FIGS. 22A-B are side and perspective views, respectively, depicting a normal spinal column.
Figure 22A:
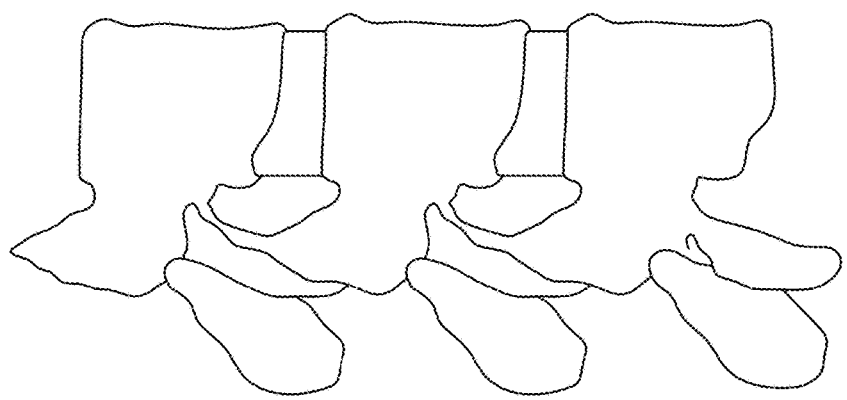
Figure 23B:
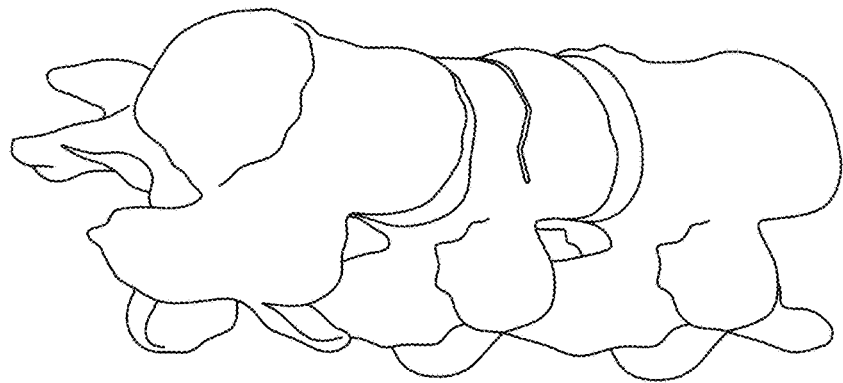
FIGS. 23A-B are side and perspective views, respectively, depicting a spinal column with a fracture in one vertebrae.
Figure 23A:
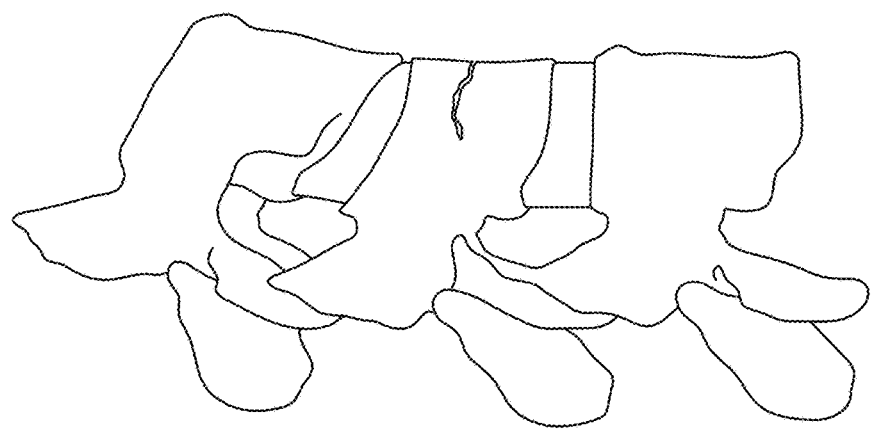

FIG. 21 shows the distal leg bonding process setup where expandable member 150 has been placed in a proximal position to a proximal heat shield 172 (sub-step 1202 of FIG. 10). In the example embodiment heat shrink tubing 160 is advanced proximally around distal leg 156 (sub-step 1204 of FIG. 10). Expandable member 150 can be adjacent and touching proximal heat shield 172. In this configuration heat shrink tubing 160 should be exposed at the distal side of proximal heat shield 172 for heat treatment from heating element 170 which can be adjusted such that it touches heat shrink tubing 160. Shrink tubing 160 can extend slightly past proximal heat shield 172. In the example embodiment this slight extension is 1 mm or less. Expandable member 150 can be protected by proximal heat shield 172 while distal leg 156 is exposed for heat treatment within heat shrink tubing 160 (sub-step 1206 of FIG. 10). Once bonded, heat shrink tubing 160 can be removed (sub-step 1208 of FIG. 10) and replaced with another, smaller heat shrink tubing 160 and the process repeated once, twice, or as many times as needed to achieve the desired size and shape. Distal leg bonding process can bond distal leg 156 to third tube 130 and second tube 120 at distal coupling location 151 (FIG. 4). In some embodiments, the distal leg bond can be sufficient to allow bonded distal leg 156, second tube 120 and third tube 130 to be trimmed to 0.5 mm length from expandable member 150. This short length can provide a medical professional with additional precision in performing medical procedures with expandable member 150.

In certain embodiments, expandable member 150 and third tube 130 (including proximal tube 131 and distal tube 132 when present) are constructed of pellethane. Although the embodiments disclosed herein are not limited to pellethane, it has been found that pellethane exhibits superior characteristics that make it highly suitable for use as these components. Pellethane exhibits the appropriate elasticity for use as the expandable member. Pellethane also has a melting temperature, viscosity when melted, and adhesive (and cohesive) characteristics that are suitable for bonding third tube 130 to expandable member 150, first tube 110, mandrel 140, and second tube 120 (as well as for bonding proximal tube 131 to distal tube 132 in those embodiments). The use of pellethane for third tube 130 can significantly facilitate the creation of the bond with mandrel 140, as that bond can be as short as 1 mm or less in certain embodiments. Although different pellethanes can be used, it has been found that pellethane 90A exhibits optimal performance in certain embodiments.

Figure 24:
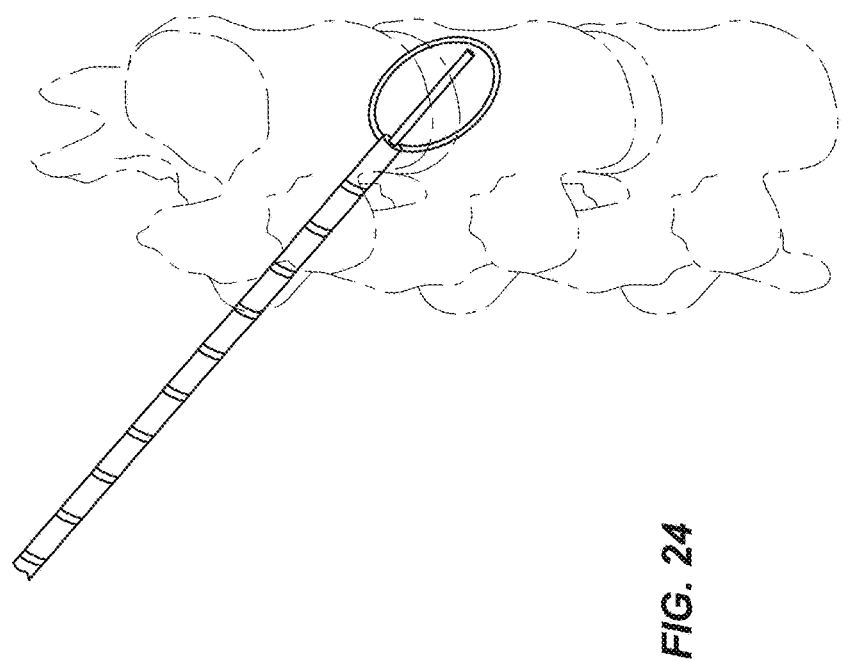
FIGS. 24-25 are partial cross-sectional views depicting an example embodiment of the catheter device with the expandable member inflated within a spinal column to compress cancellous bone.
Figure 25:
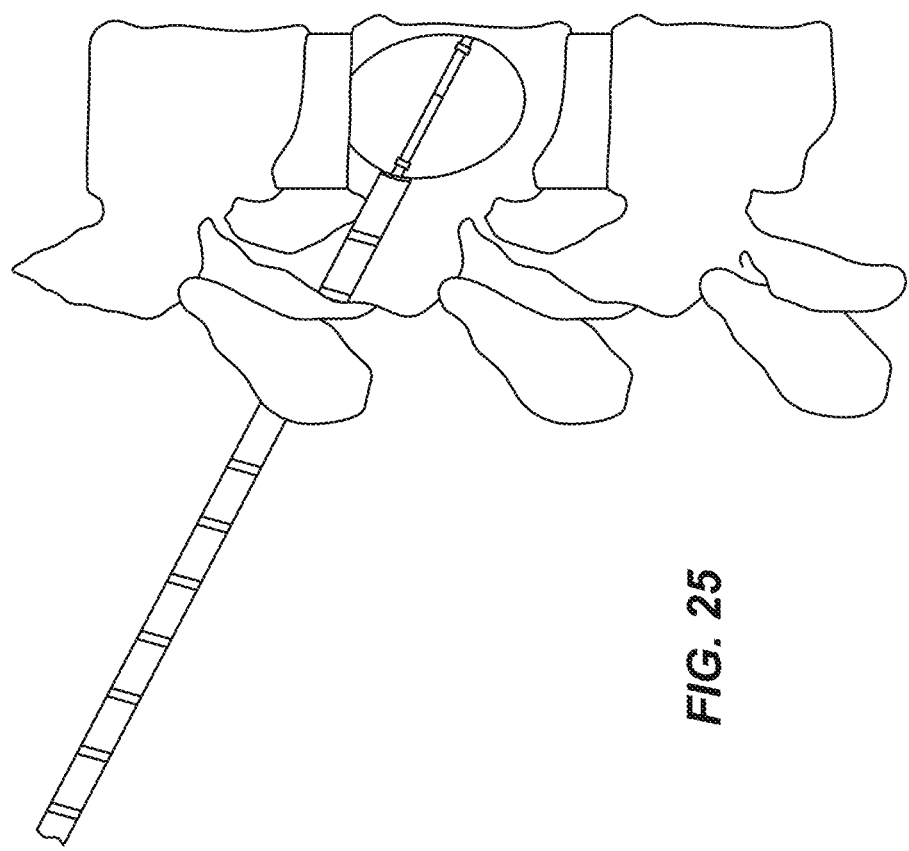
Figure 26:
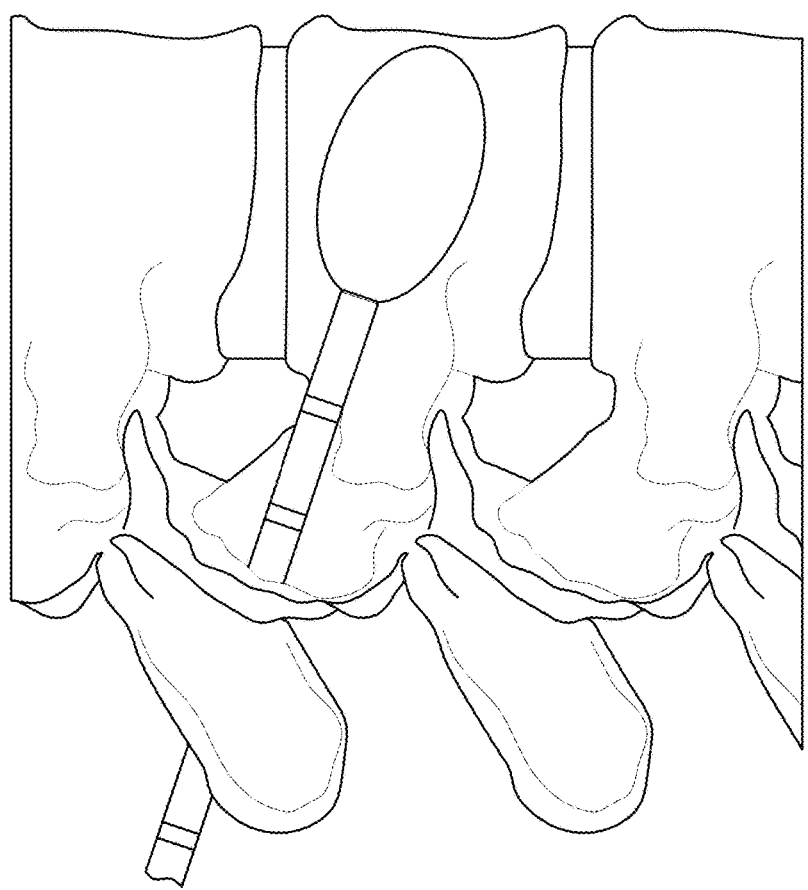
FIG. 26 is a partial cross-sectional view depicting an example embodiment of the catheter device with bone cement injected into a space within the spinal column after deteriorating cancellous bone has been compressed.

FIGS. 22-26 show an example embodiment of a procedure using the apparatus described herein. FIGS. 22A-B show an example embodiment of a side perspective and angled perspective of a normal spinal column. FIGS. 23A-B shows an example embodiment of a side perspective and angled perspective of a spinal column with a fracture 180 in one vertebrae. This type of fracture may be more likely to occur for example if cancellous bone within the vertebrae deteriorates and no procedure is performed to reinforce the bone using an apparatus as described herein. FIGS. 24-25 show an example embodiment of a spinal column wireframe and diagram respectively with expandable member 150 inflated within the bone to compress cancellous bone. FIG. 26 shows an example embodiment of a spinal column diagram with bone cement injected into the bone after deteriorating cancellous bone has been compressed using the apparatus described herein.

Where a range of values is provided, it is noted that each intervening value, to the tenth of the unit of the lower limit unless the context clearly dictates otherwise, between the upper and lower limit of that range and any other stated or intervening value in that stated range, is encompassed within the disclosure and can be claimed as an sole value or as a smaller range. Where the stated range includes one or both of the limits, ranges excluding either or both of those included limits are also included in the disclosure.

Where a discrete value or range of values is provided, it is noted that that value or range of values may be claimed more broadly than as a discrete number or range of numbers, unless indicated otherwise. For example, each value or range of values provided herein may be claimed as an approximation and this paragraph serves as antecedent basis and written support for the introduction of claims, at any time, that recite each such value or range of values as "approximately" that value, "approximately" that range of values, "about" that value, and/or "about" that range of values. Conversely, if a value or range of values is stated as an approximation or generalization, e.g., approximately X or about X, then that value or range of values can be claimed discretely without using such a broadening term.

However, in no way should a claim be limited to a particular value or range of values absent explicit recitation of that value or range of values in the claims. Values and ranges of values are provided herein merely as examples.

While the embodiments are susceptible to various modifications and alternative forms, specific examples thereof have been shown in the drawings and are herein described in detail. It should be understood, however, that these embodiments are not to be limited to the particular form disclosed, but to the contrary, these embodiments are to cover all modifications, equivalents, and alternatives falling within the spirit of the disclosure. Furthermore, any features, functions, steps, or elements of the embodiments may be recited in or added to the claims, as well as negative limitations that define the inventive scope of the claims by features, functions, steps, or elements that are not within that scope.

What is claimed is:

1. An apparatus for compacting cancellous bone during a procedure comprising:
   a first tube with a beveled distal end;
   a second tube with a proximal end distal to the beveled distal end of the first tube;
   a third tube in which the first tube and second tube are located; and
   an expandable member with a proximal end secured proximal to the beveled distal end of the first tube and a distal end secured distal to the proximal end of the second tube;
   wherein the first tube is operable to deliver inflation medium into the expandable member through the beveled distal end, and
   wherein the second tube moves in a distal direction from the beveled distal end of the first tube during inflation of the expandable member.

2. The apparatus of claim 1, wherein the third tube is bonded to the expandable member.

3. The apparatus of claim 1, wherein the third tube is pellethane.

4. The apparatus of claim 1, wherein the second tube moves in a proximal direction toward the beveled distal end of the first tube during deflation of the expandable member.

5. The apparatus of claim 1, wherein the expandable member expands in a longitudinal direction in addition to a radial direction upon inflation.

6. The apparatus of claim 1, wherein inflation medium is introduced into an interior of the balloon using an actuator.

7. The apparatus of claim 1, wherein first and second ends of the expandable member are bonded directly to the third tube.

8. The apparatus of claim 1, wherein the third tube is elastic and stretches during inflation of the expandable member and contracts during deflation of the expandable member.

9. The apparatus of claim 1, wherein the balloon has a plurality of pleats.

10. The apparatus of claim 1, further comprising a shim.

* * * * *